United States Patent
Zhang et al.

(10) Patent No.: US 10,876,089 B2
(45) Date of Patent: Dec. 29, 2020

(54) APPARATUS AND METHOD FOR HIGH-FIDELITY PODOCYTE CULTIVATION

(71) Applicants: Boyang Zhang, Toronto (CA); Anastasia Korolj, Toronto (CA); Carol Laschinger, Toronto (CA); Milica Radisic, Toronto (CA)

(72) Inventors: Boyang Zhang, Toronto (CA); Anastasia Korolj, Toronto (CA); Carol Laschinger, Toronto (CA); Milica Radisic, Toronto (CA)

(73) Assignees: Boyang Zhang, Toronto (CA); Anastasia Korolj, Toronto (CA); Carol Laschinger, Toronto (CA); Milica Radisic, Toronto (CA)

( * ) Notice: Subject to any disclaimer, the term of this patent is extended or adjusted under 35 U.S.C. 154(b) by 98 days.

(21) Appl. No.: 15/724,731

(22) Filed: Oct. 4, 2017

(65) Prior Publication Data

US 2018/0127701 A1 May 10, 2018

Related U.S. Application Data

(60) Provisional application No. 62/404,693, filed on Oct. 5, 2016.

(51) Int. Cl.
*C12M 1/12* (2006.01)
*C12M 1/00* (2006.01)
(Continued)

(52) U.S. Cl.
CPC .............. *C12M 25/04* (2013.01); *B29C 35/02* (2013.01); *B29C 37/0053* (2013.01);
(Continued)

(58) Field of Classification Search
CPC ...... C12M 25/04; C12M 23/02; C12M 25/00; C12M 23/20; C12M 23/12; B29C 35/02;
(Continued)

(56) References Cited

U.S. PATENT DOCUMENTS 5,266,476 A * 11/1993 Sussman .............. C12N 5/0068
435/179
2006/0147903 A1 * 7/2006 Li .......................... C12M 21/08
435/4

(Continued)

OTHER PUBLICATIONS

Burghardt T, Hochapfel F, Salecker B, Meese C, Grone HJ, Rachel R, et al. "Advanced electron microscopic techniques provide a deeper insight into the peculiar features of podocytes". American journal of physiology Renal physiology. 2015;309(12):F1082-9.

(Continued)

*Primary Examiner* — Michael L Hobbs
(74) *Attorney, Agent, or Firm* — Ridout & Maybee LLP

(57) ABSTRACT

An apparatus for cultivation of cells, particularly podocytes, is described. The apparatus includes a cell cultivation surface exhibiting at least one feature providing a non-planar microtopology. A method for cultivation of cells, particularly podocytes, is also described. The method includes introducing a differentiation media including ATRA, Vit D3, and Dex.

23 Claims, 23 Drawing Sheets

(51) Int. Cl.
*C12N 5/071* (2010.01)
*B29C 35/02* (2006.01)
*B29C 37/00* (2006.01)
*B29C 39/02* (2006.01)
*C12M 1/32* (2006.01)
*B29C 59/02* (2006.01)
*B29C 35/08* (2006.01)

(52) U.S. Cl.
CPC .......... *B29C 39/026* (2013.01); *C12M 23/02* (2013.01); *C12M 23/12* (2013.01); *C12M 23/20* (2013.01); *C12M 25/00* (2013.01); *C12N 5/0686* (2013.01); *B29C 2035/0827* (2013.01); *B29C 2059/023* (2013.01); *B29C 2059/028* (2013.01); *C12N 2500/38* (2013.01); *C12N 2501/38* (2013.01); *C12N 2501/385* (2013.01); *C12N 2501/39* (2013.01); *C12N 2513/00* (2013.01)

(58) Field of Classification Search
CPC ........ B29C 2059/028; B29C 2059/023; B29C 39/026; B29C 37/0053; B29C 2035/082; C12N 5/0686; C12N 2501/39; C12N 2501/38; C12N 2501/385; C12N 2513/00; C12N 2500/38
See application file for complete search history.

(56) References Cited

U.S. PATENT DOCUMENTS

| | | | |
|---|---|---|---|
| 2009/0017540 A1* | 1/2009 | Nishio | C12M 25/06 435/395 |
| 2013/0045535 A1* | 2/2013 | Soen | C12M 21/08 435/395 |

OTHER PUBLICATIONS

Shankland SJ, Pippin JW, Reiser J, Mundel P. "Podocytes in culture: past, present, and future". Kidney Int. 2007;72(1):26-36.
Li M, Corbelli A, Watanabe S, Armelloni S, Ikehata M, Parazzi V, et al. "Three-dimensional podocyte-endothelial cell co-cultures: Assembly, validation, and application to drug testing and intercellular signaling studies". European journal of pharmaceutical sciences : official journal of the European Federation for Pharmaceutical Sciences. 2016;86:1-12.
Bruggeman LA, Doan RP, Loftis J, Darr A, Calabro A. "A cell culture system for the structure and hydrogel properties of basement membranes; Application to capillary walls". Cellular and molecular bioengineering. 2012;5(2):194-204.
Ransom RF, Lam NG, Hallett MA, Atkinson SJ, Smoyer WE. "Glucocorticoids protect and enhance recovery of cultured murine podocytes via actin filament stabilization". Kidney Int. 2005;68(6):2473-83.
Vaughan MR, Pippin JW, Griffin SV, Krofft R, Fleet M, Haseley L, et al. "ATRA induces podocyte differentiation and alters nephrin and podocin expression in vitro and in vivo". Kidney Int. 2005;68(1):133-44.
Takano Y, Yamauchi K, Hiramatsu N, Kasai A, Hayakawa K, Yokouchi M, et al. "Recovery and maintenance of nephrin expression in cultured podocytes and identification of HGF as a repressor of nephrin". American journal of physiology Renal physiology. 2007;292(5):F1573-82.
Chittiprol S, Chen P, Petrovic-Djergovic D, Eichler T, Ransom RF. "Marker expression, behaviors, and responses vary in different lines of conditionally immortalized cultured podocytes". American journal of physiology Renal physiology. 2011;301(3):F660-71.
Schiwek D, Endlich N, Holzman L, Holthofer H, Kriz W, Endlich K. "Stable expression of nephrin and localization to cell-cell contacts in novel murine podocyte cell lines". Kidney Int. 2004;66(1):91-101.
Takasato M, Pei XE, Chiu HS, Maier B, Baillie GJ, Ferguson C, et al. "Kidney organoids from human iPS cells contain multiple lineages and model human nephrogenesis". Nature. 2015;526(7574):564-8.
Kawachi H, Miyauchi N, Suzuki K, Han GD, Orikasa M, Shimizu F. "Role of podocyte slit diaphragm as a filtration barrier". Nephrology (Carlton). 2006;11(4):274-81.
Brinkkoetter PT, Ising C, Benzing T. "The role of the podocyte in albumin filtration". Nature reviews Nephrology. 2013;9(6):328-36.
Herman-Edelstein M, Thomas MC, Thallas-Bonke V, Saleem M, Cooper ME, Kantharidis P. "Dedifferentiation of immortalized human podocytes in response to transforming growth factor-beta: a model for diabetic podocytopathy". Diabetes. 2011;60(6):1779-88.
Obregon R, Ramon-Azcon J, Ahadian S, Shiku H, Bae H, Ramalingam M, et al. "The use of microtechnology and nanotechnology in fabricating vascularized tissues". Journal of nanoscience and nanotechnology. 2014;14(1):487-500.
Au HTH, Cheng I, Chowdhury MF, Radisic M. "Interactive effects of surface topography and pulsatile electrical field stimulation on orientation and elongation of fibroblasts and cardiomyocytes". Biomaterials. 2007;28(29):4277-93.
Chiu LLY, Montgomery M, Liang Y, Liu H, Radisic M. "Perfusable branching microvessel bed for vascularization of engineered tissues". Proceedings of the National Academy of Sciences of the United States of America. 2012;109(50): E3414-E23.
Zhang B, Montgomery M, Chamberlain MD, Ogawa S. Korolj A, Pahnke A, et al. "Biodegradable scaffold with built-in vasculature for organ-on-a-chip engineering and direct surgical anastomosis". Nature materials. 2016.
Pahnke A, Montgomery M, Radisic M. "Spatial and Electrical Factors Regulating Cardiac Regeneration and Assembly". 2015:71-92.
Engelmayr GC, Jr., Cheng M, Bettinger CJ, Borenstein JT, Langer R, Freed LE. "Accordion-like honeycombs for tissue engineering of cardiac anisotropy". Nature materials. 2008;7(12):1003-10.
Zhang B, Montgomery M, Davenport-Huyer L, Korolj A, Radisic M. "Platform technology for scalable assembly of instantaneously functional mosaic tissues". Science Advances. 2015;1(7).
Bhatia SN, Ingber DE. "Microfluidic organs-on-chips". Nature biotechnology. 2014;32(8):760-72.
Mu X, Zheng W, Xiao L, Zhang W, Jiang X. "Engineering a 3D vascular network in hydrogel for mimicking a nephron". Lab on a Chip. 2013;13(8):1612.
Li M, Hakimi N, Perez R, Waldman S, Kozinski JA, Hwang DK. "Microarchitecture for a three-dimensional wrinkled surface platform". Advanced materials (Deerfield Beach, Fla). 2015;27(11):1880-6.
Kang E, Shin S-J, Lee KH, Lee S-H. "Novel PDMS cylindrical channels that generate coaxial flow, and application to fabrication of microfibers and particles". Lab on a Chip. 2010;10(14):1856-61.
Park JY, Lee DH, Lee EJ, Lee S-H. "Study of cellular behaviors on concave and convex microstructures fabricated from elastic PDMS membranes". Lab on a Chip. 2009;9(14):2043-9.
Hosseini V, Kollmannsberger P, Ahadian S, Ostrovidov S, Kaji H, Vogel V, et al. "Fiber-assisted molding (FAM) of surfaces with tunable curvature to guide cell alignment and complex tissue architecture". Small (Weinheim an der Bergstrasse, Germany). 2014;10(23):4851-7.
Yevick HG, Duclos G, Bonnet I, Silberzan P. "Architecture and migration of an epithelium on a cylindrical wire". Proceedings of the National Academy of Sciences of the United States of America. 2015;112(19):5944-9.
Schmittgen TD, Livak KJ. "Analyzing real-time PCR data by the comparative CT method". Nature Protocols. 2008;3(6):1101-8.
Guan N, Ding J, Deng J, Zhang J, Yang J. "Key molecular events in puromycin aminonucleoside nephrosis rats". Pathology international. 2004;54(9):703-11.
Wiedeman MP. "Dimensions of blood vessels from distributing artery to collecting vein". Circulation Research. 1963;12(4):375-8.
Versaevel M, Grevesse T, Gabriele S. "Spatial coordination between cell and nuclear shape within micropatterned endothelial cells". Nat Commun. 2012;3:671.

(56) References Cited

OTHER PUBLICATIONS

George B, Verma R, Soofi AA, Garg P, Zhang J, Park TJ, et al. "Crk1/2-dependent signaling is necessary for podocyte foot process spreading in mouse models of glomerular disease". The Journal of clinical investigation. 2012;122(2):674-92.

Schwarz K, Simons M, Reiser J, Saleem MA, Faul C, Kriz W, et al. "Podocin, a raft-associated component of the glomerular slit diaphragm, interacts with CD2AP and nephrin". The Journal of clinical investigation. 2001;108(11):1621-9.

Garg P, Holzman LB. "Podocytes: gaining a foothold". Experimental cell research. 2012;318(9):955-63.

Von Philipsborn AC, Lang S, Bernard A, Loeschinger J, David C, Lehnert D, et al. "Microcontact printing of axon guidance molecules for generation of graded patterns". Nat Protocols. 2006;1(3):1322-8.

Saleem MA, O'Hare MJ, Reiser J, Coward RJ, Inward CD, Farren T, et al. "A Conditionally Immortalized Human Podocyte Cell Line Demonstrating Nephrin and Podocin Expression". Journal of the American Society of Nephrology. 2002;13(3):630-8.

Haraldsson B, Nystrom J, Deen WM. "Properties of the glomerular barrier and mechanisms of proteinuria". Physiol Rev. 2008;88(2):451-87.

Davenport Huyer L, Zhang B, Korolj A, Montgomery M, Drecun S, Conant G, et al. "Highly Elastic and Moldable Polyester Biomaterial for Cardiac Tissue Engineering Applications". ACS Biomaterials Science & Engineering. 2016;2(5):780-8.

Zhang B, Montgomery M, Chamberlain MD, Ogawa S. Korolj A, Pahnke A, et al. "Biodegradable scaffold with built-in vasculature for organ-on-a-chip engineering and direct surgical anastomosis". Nat Mater 2016;15(6):669-78.

Gaillard PJ, Voorwinden LH, Nielsen JL, Ivanov A, Atsumi R, Engman H, et al. "Establishment and functional characterization of an in vitro model of the blood-brain barrier, comprising a co-culture of brain capillary endothelial cells and astrocytes". Eur J Pharm Sci. 2001;12(3):215-22.

Yuan W, Lv Y, Zeng M, Fu BM. "Non-invasive measurement of solute permeability in cerebral microvessels of the rat". Microvascular research. 2009;77(2):166-73.

Zadpoor AA. "Bone tissue regeneration: the role of scaffold geometry". Biomaterials science. 2015;3(2):231-45.

Unger, M. A., Chou, H. P., Thorsen, T., Scherer, A. & Quake, S. R., "Monolithic microfabricated valves and pumps by multilayer soft lithography", Science 288, 113-116 (2000).

\* cited by examiner

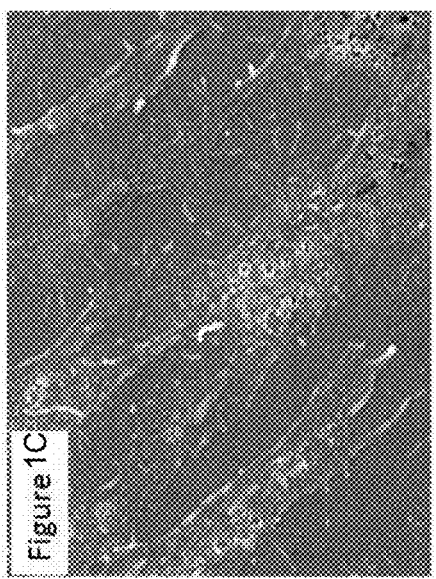
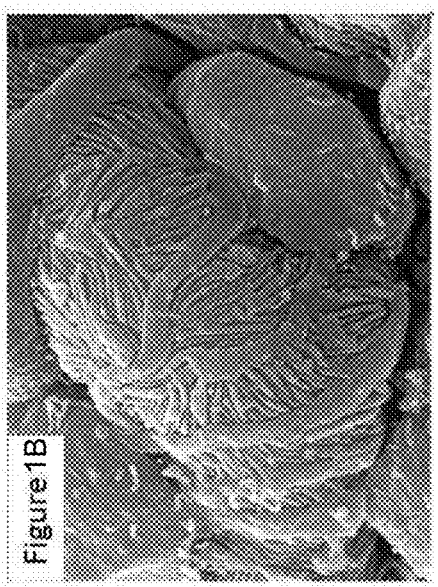
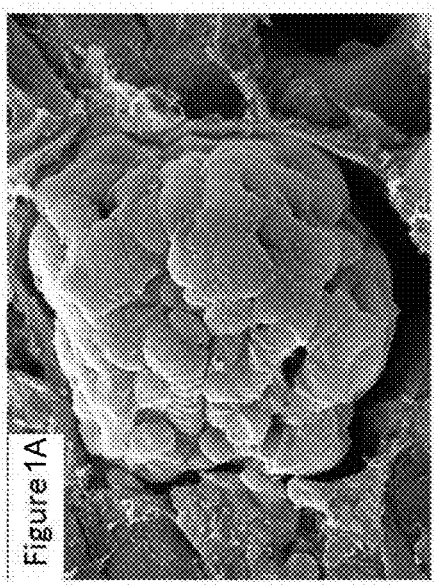

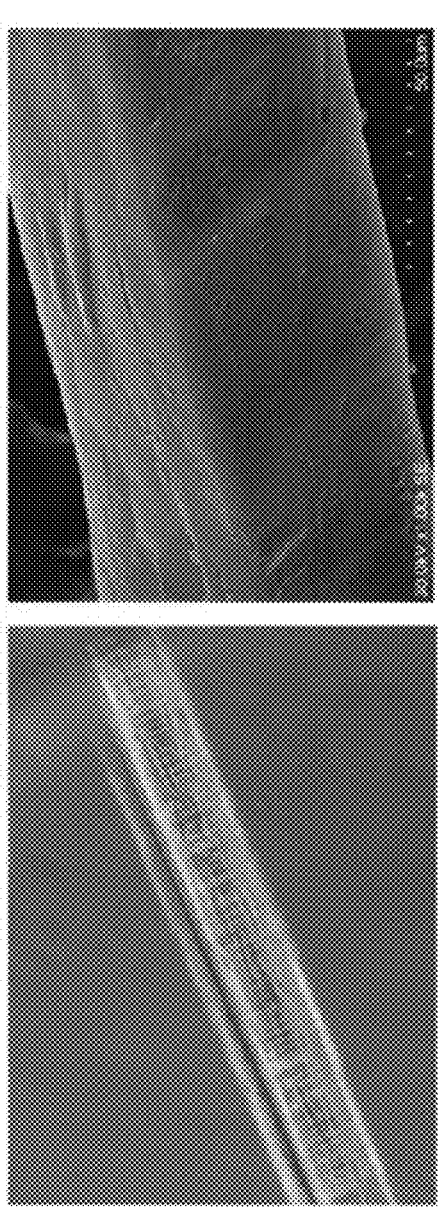
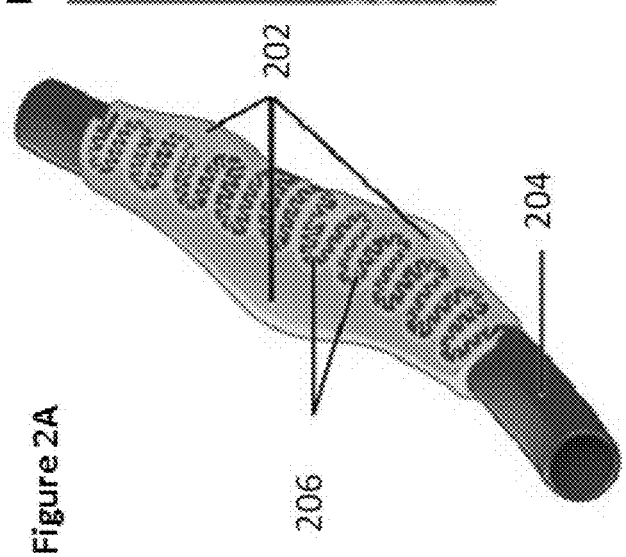
Figure 2B
Figure 2A

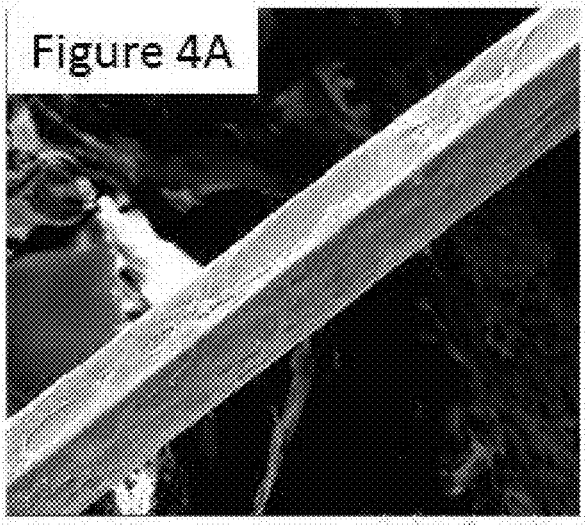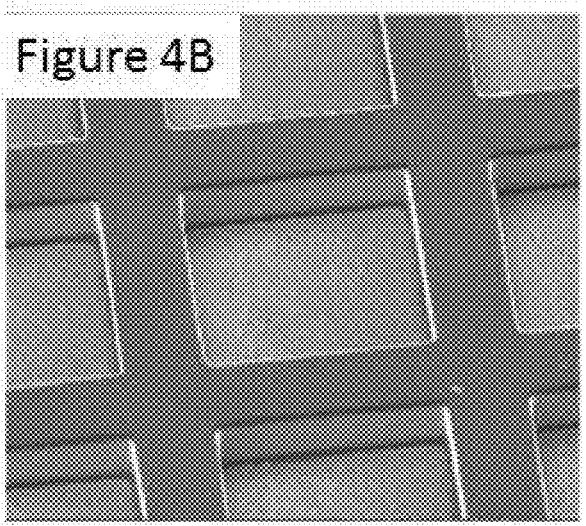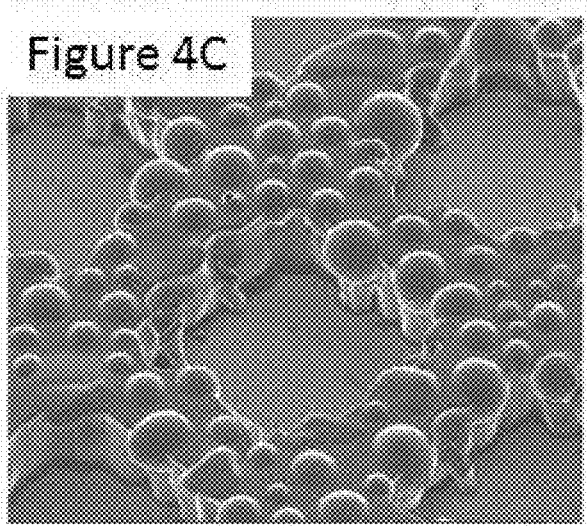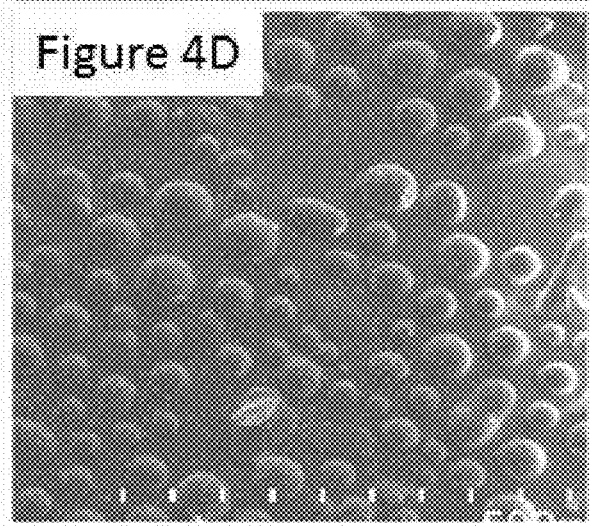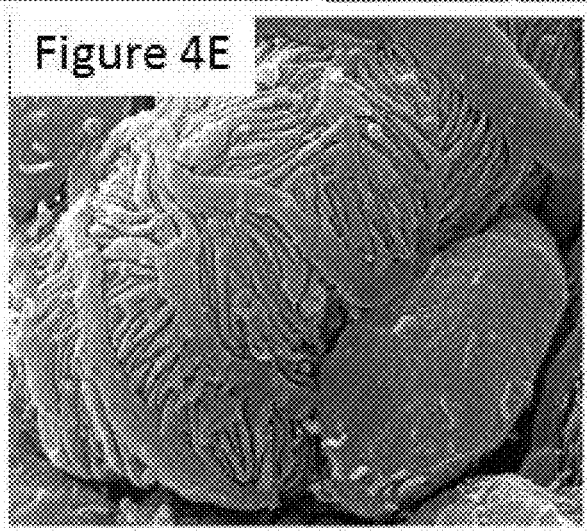

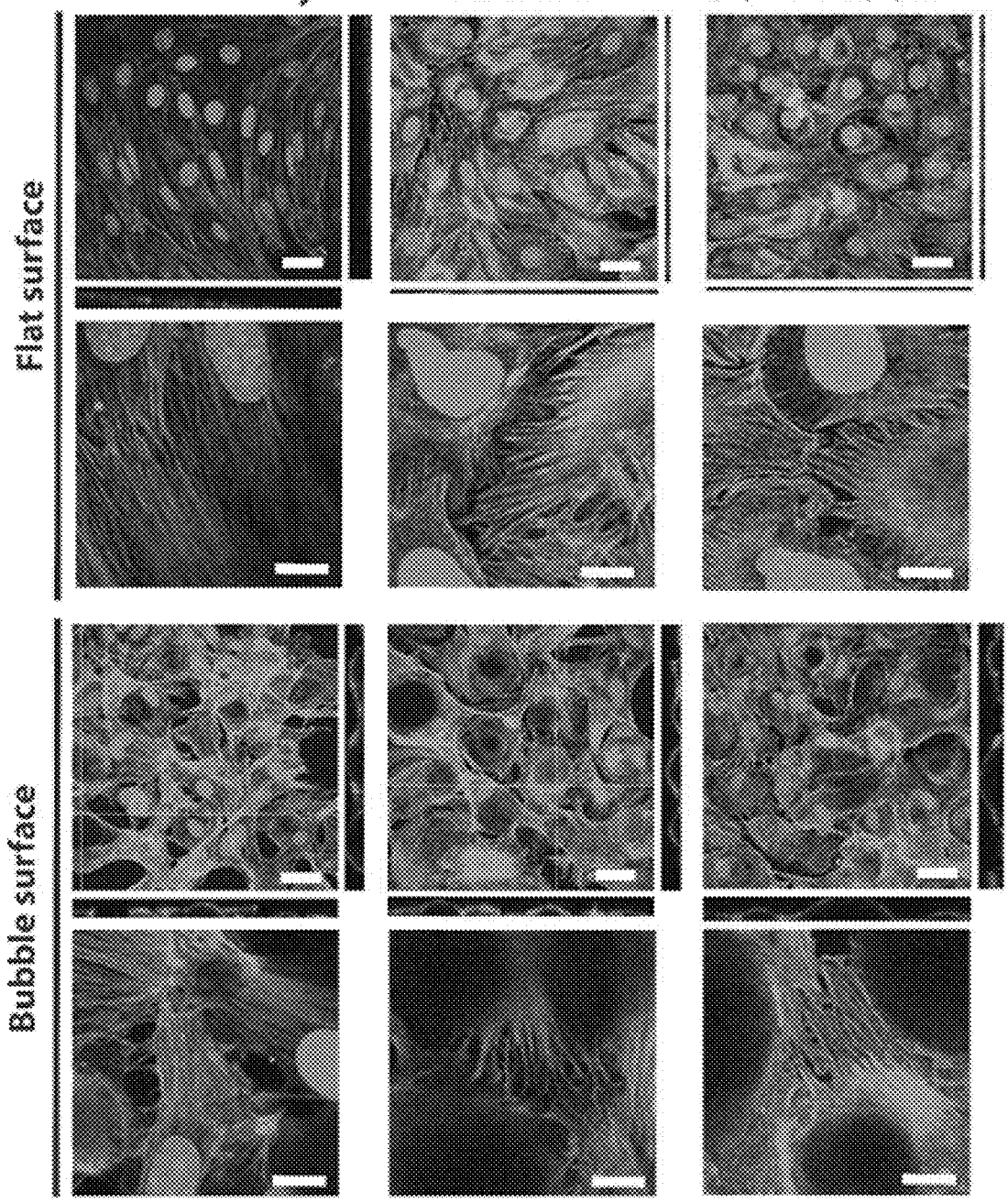

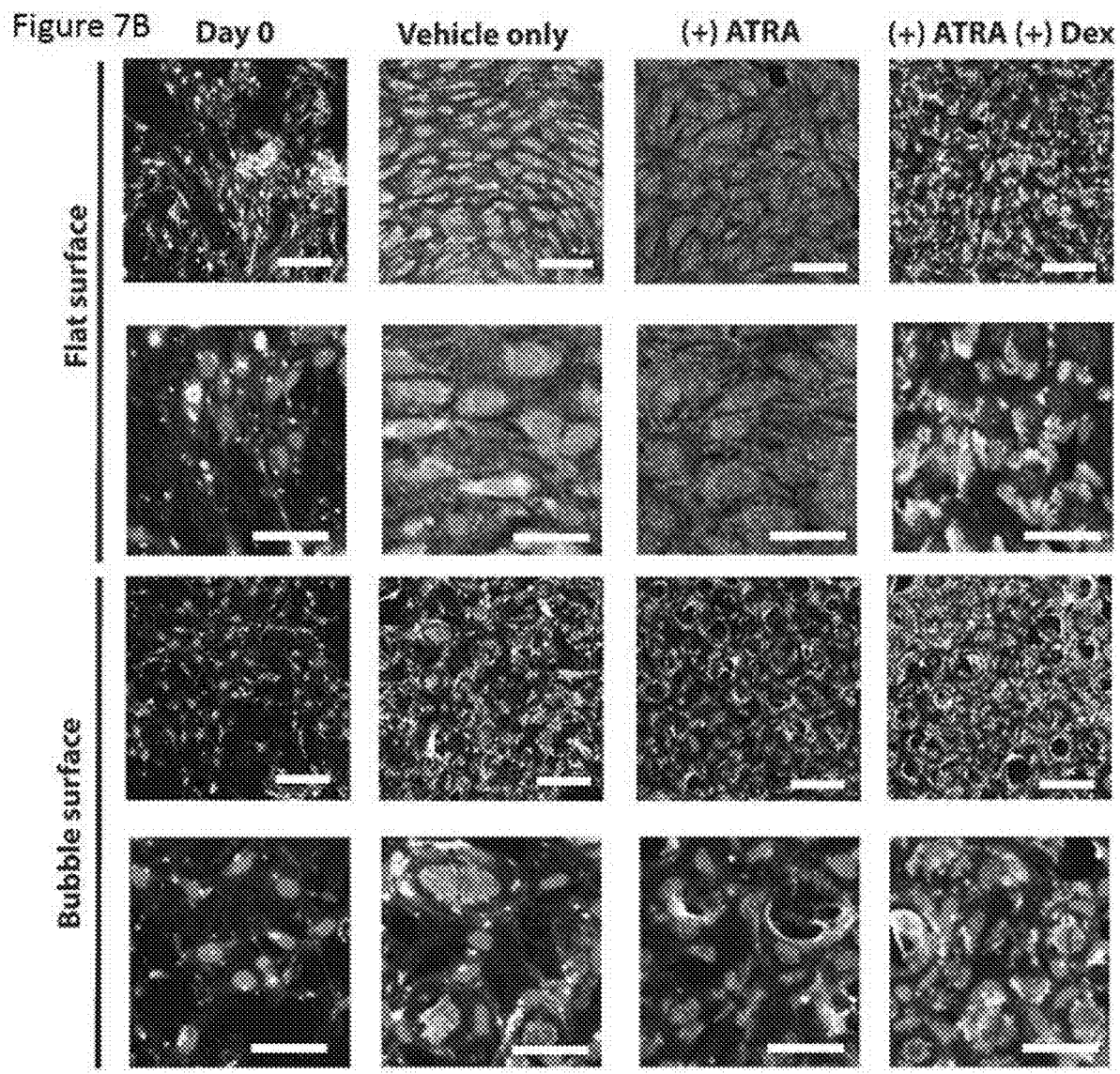

Figure 7C Flat surface        Bubble surface
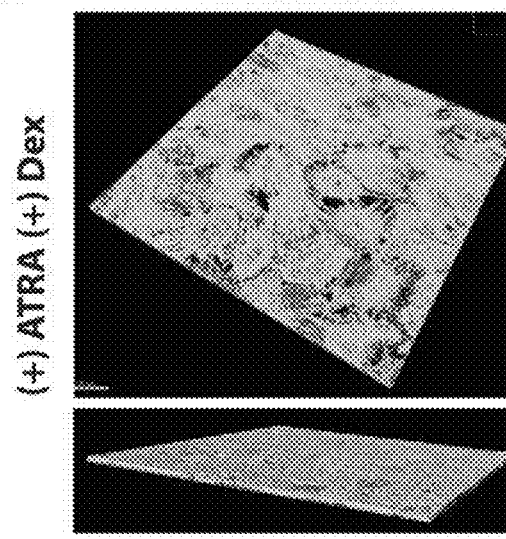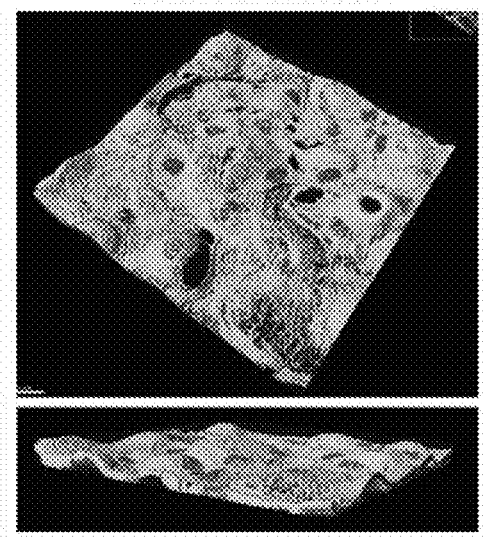
Figure 7D Flat surface        Bubble surface
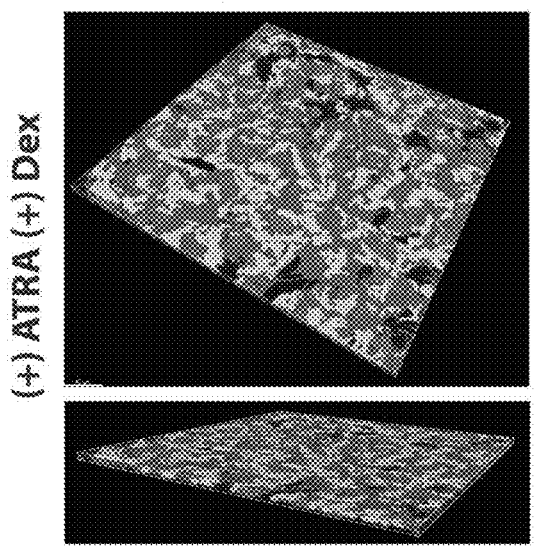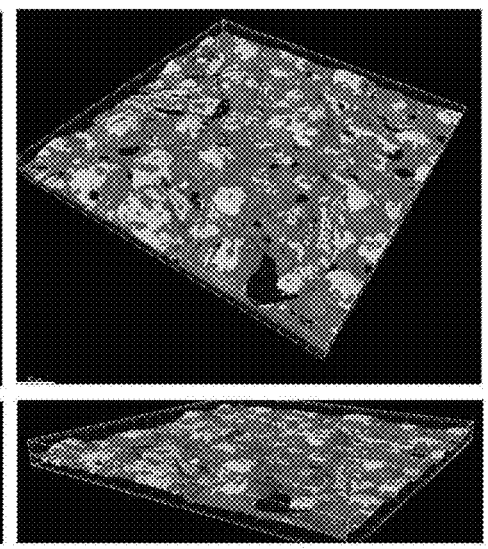

Figure 8A
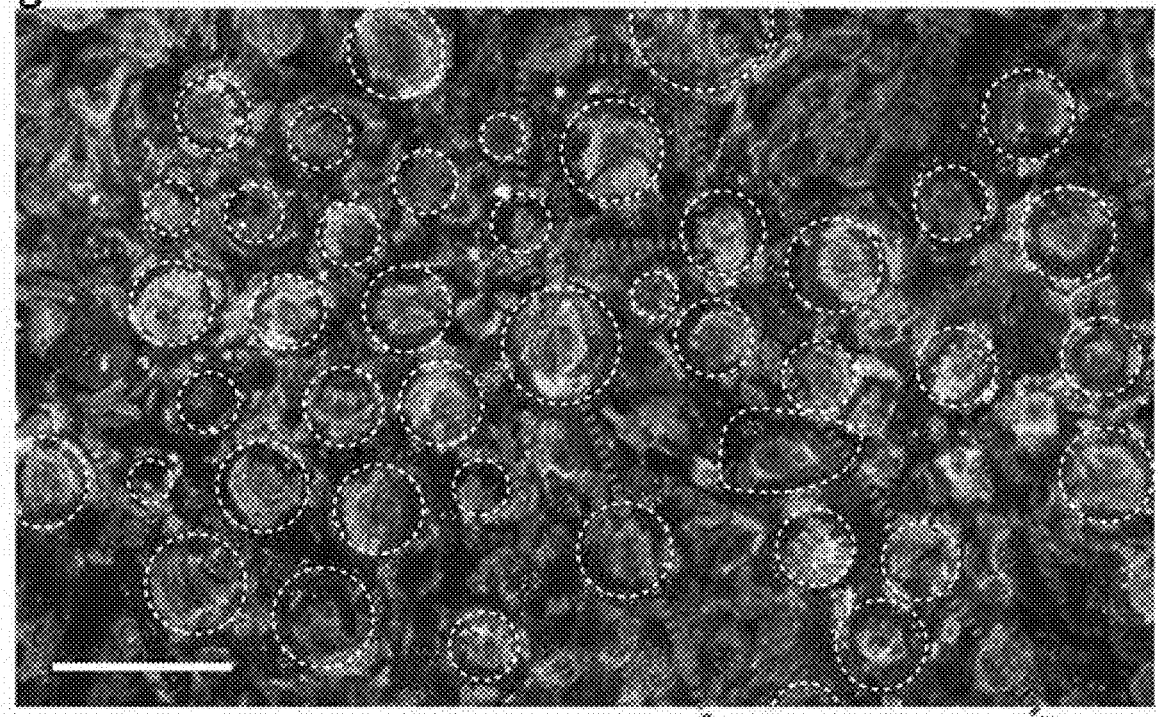
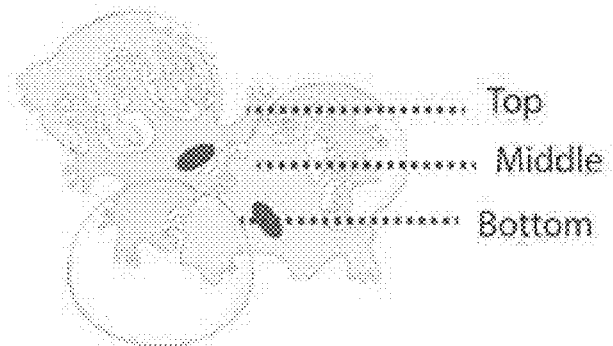
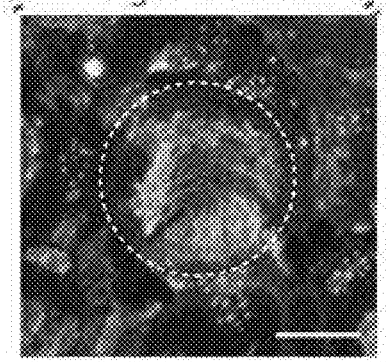
Merged Z-stack
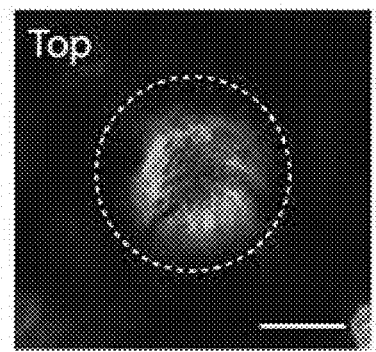
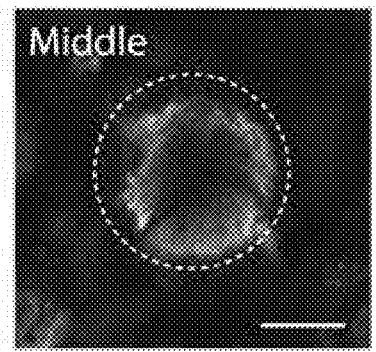
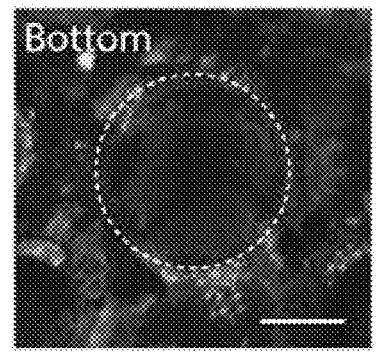

Flat surface

Bubble surface

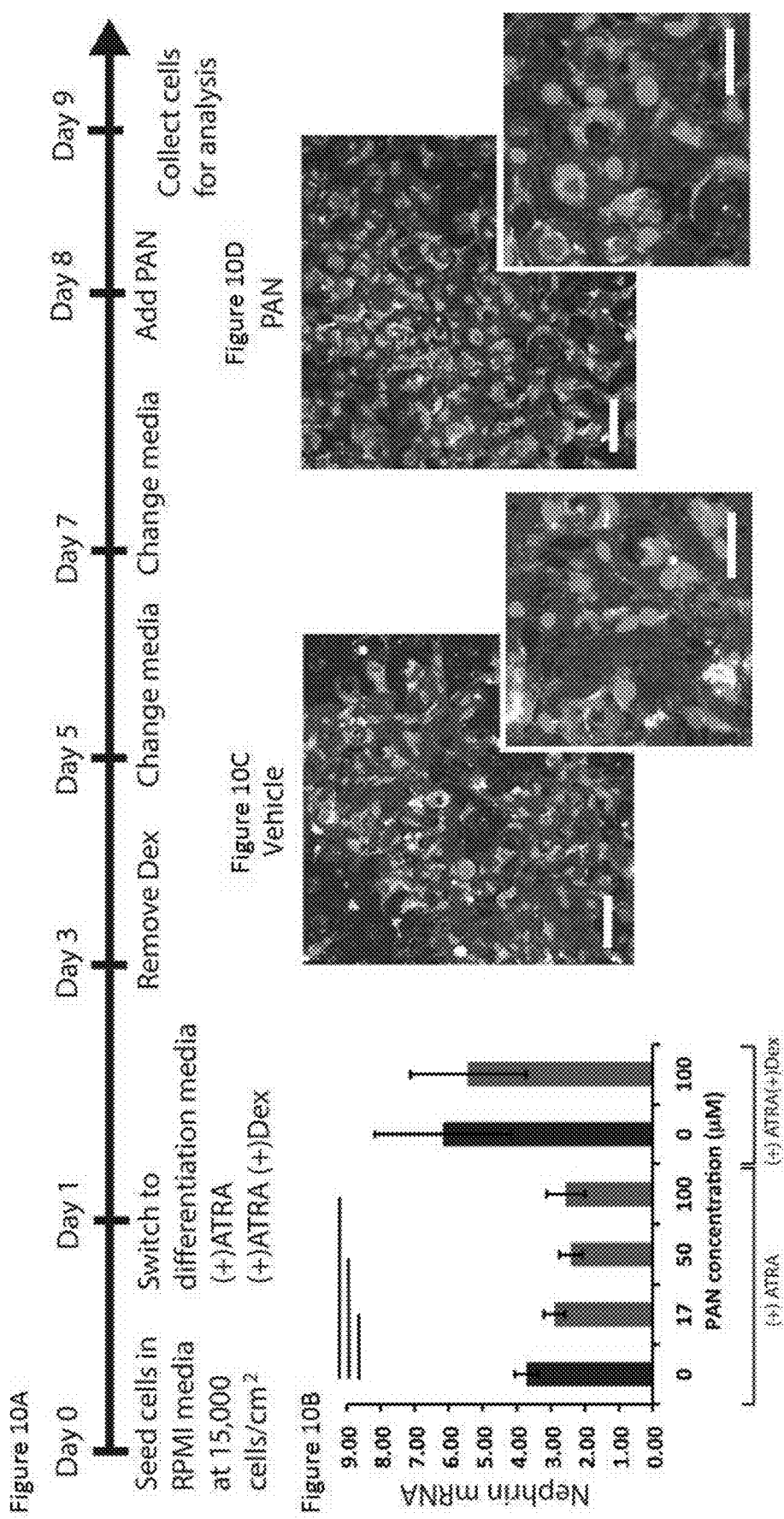

APPARATUS AND METHOD FOR HIGH-FIDELITY PODOCYTE CULTIVATION

CROSS-REFERENCE TO RELATED APPLICATIONS

The present disclosure claims priority from U.S. provisional patent application No. 62/404,693, entitled "BIOMIMETIC 3D PLATFORM INDUCES NEPHRIN UPREGULATION IN DIFFERENTIATING PODOCYTES IN VITRO", filed Oct. 5, 2016, the entirety of which is hereby incorporated by reference.

FIELD

The present disclosure relates to cultivation of podocytes. In particular, the present disclosure relates to three-dimensional structure and biochemical stimulation for promoting high-fidelity podocyte cultivation.

BACKGROUND

The kidney nephron is the biological unit in which waste is filtered from the blood into the urine. In the nephron's glomerulus, podocytes wrap around a dense cluster of capillaries on the urinary side, sitting atop of the glomerular basement membrane and fenestrated endothelium (blood side). This tripartite structure forms the functional filtration unit. The podocyte is a highly specialized epithelial cell that surrounds the glomerular capillaries in the kidneys and provides a filtration barrier to limit the passage of high molecular weight proteins. This barrier function is determined by specialized protein complexes called slit diaphragms that are localized along interdigitated podocyte-podocyte contacts (1). Podocytes also possess paracrine actions that maintain the normal structure and function of the glomerulus, e.g. mesangial structure, through signalling and secretion of various hormones and growth factors.

Unfortunately, the barrier function of podocytes has been poorly studied because conventional in vitro podocyte cultures do not form slit diaphragms. That is, conventional methods for cultivating podocytes in vitro result in cultures that lack the filtration barrier unit. Thus, conventional in vitro cell culture techniques do not provide high-fidelity cultivation of podocytes. Conventional monolayer culture fails to capture key phenotypical characteristics of podocytes. Therefore, it has been difficult if not impossible to study these aspects of podocyte physiology in vitro. This means that new potentially promising compounds cannot be screened correctly for either their positive or negative effects on key podocyte function.

SUMMARY

The present disclosure describes examples of biomimetic, microfabricated platforms having three-dimensional features to induce functional differentiation of various cell types, including epithelial podocytes, a cell type found in the kidney nephron. The present disclosure may also be useful for any other cells that respond favorably to a non-planar cultivation surface. For example, alveolar cells, intestinal cells, thyroid cells, fat cells or any other tissue having a curved or irregular topology may be cultivated using the disclosed methods and apparatuses. The present disclosure also describes example methods of cultivating cells by introducing biochemical cues during cultivation, to promote differentiation.

In some examples, the present disclosure describes an apparatus for cultivation of cells. The apparatus includes a first chamber for cultivating cells. The apparatus also includes a surface, supported in the first chamber, for cell cultivation thereon. The surface exhibits at least one feature having a non-planar microtopology, such as a concave or convex microcurvature, or the outer surfaces of a strand or mesh.

In some examples, the present disclosure describes a method for cultivating cells. The method includes seeding podocytes on a cell cultivation surface at a seeding density. The method also includes introducing differentiation media to the podocytes. The differentiation media includes all-trans-retinoic acid (ATRA), 1,25-dihydroxyvitamin D3 (Vit D3), and dexamethasone (Dex). The method also includes removal of Dex from the differentiation media after a first time duration. The method also includes obtaining cultivated cells after a second time duration. In some examples, the method may include using the apparatus described above for cultivating cells.

In some aspects, the present disclosure provides an apparatus for cultivation of cells. The apparatus includes a first chamber for cultivating cells. The apparatus also includes a surface, supported in the first chamber, for cell cultivation thereon. The surface exhibits at least one microcurvature providing a non-planar microtopology.

In some examples of any of the preceding aspects/embodiments, the at least one microcurvature is a convex microcurvature.

In some examples of any of the preceding aspects/embodiments, the at least one microcurvature is a concave microcurvature.

In some examples of any of the preceding aspects/embodiments, the first chamber has an opening defined therein to permit access to a second chamber, and the surface is positioned over the opening and has a porosity to enable at least partial access to the second chamber.

In some examples of any of the preceding aspects/embodiments, the porosity is about 40%.

In some examples of any of the preceding aspects/embodiments, the surface includes a first side exhibiting a first microcurvature and an opposing second side exhibiting a second microcurvature.

In some examples of any of the preceding aspects/embodiments, the first microcurvature includes a convex microcurvature and the second microcurvature includes a concave microcurvature.

In some examples of any of the preceding aspects/embodiments, the surface includes a first side exhibiting a convex microcurvature and an opposing second side that is substantially flat.

In some examples of any of the preceding aspects/embodiments, at least one micro-hole is defined in the surface, to permit further access to the second chamber.

In some examples of any of the preceding aspects/embodiments, the at least one micro-hole has a diameter in the range of about 0.4-10 µm.

In some examples of any of the preceding aspects/embodiments, the at least one microcurvature has an average diameter of about 20-100 µm and a height of about 5-20 µm.

In some examples of any of the preceding aspects/embodiments, the at least one microcurvature has a radius of curvature of about 5, 10, 50 or 20 µm.

In some examples of any of the preceding aspects/embodiments, the surface includes a plurality of convex microcurvatures.

In some aspects, the present disclosure provides a method for cultivating cells. The method includes providing the apparatus of any of the preceding aspects/embodiments. The method also includes introducing cells onto the surface of the apparatus. The method also includes promoting differentiation of the cells.

In some examples of any of the preceding aspects/embodiments, the cells are podocytes.

In some aspects, the present disclosure provides a method for fabricating an apparatus for cultivation of cells. The method includes providing a bead-covered surface by fixing a plurality of glass beads on a substrate. The method also includes forming an inverse mold by curing a first polymer over the bead-covered surface. The method also includes forming a surface for cell cultivation by curing a second polymer using the inverse mold. The surface is formed to exhibit at least one microcurvature providing a non-planar microtopology. The method also includes supporting at least a portion of the surface in a first chamber for cultivating cells.

In some examples of any of the preceding aspects/embodiments, the plurality of glass beads includes glass beads having diameters in the range of about 10-1000 μm.

In some examples of any of the preceding aspects/embodiments, the plurality of glass beads includes glass beads having diameters of 10, 20, or 40 μm.

In some examples of any of the preceding aspects/embodiments, the plurality of glass beads includes glass beads having varying diameters.

In some examples of any of the preceding aspects/embodiments, the plurality of glass beads all have similar diameter.

In some examples of any of the preceding aspects/embodiments, the glass beads are fixed on the substrate in an organized fashion.

In some examples of any of the preceding aspects/embodiments, the glass beads are fixed on the substrate in a random fashion.

In some examples of any of the preceding aspects/embodiments, the second polymer includes polydimethylsiloxane (PDMS) or poly(octamethylene maleate (anhydride) 1,2,4-butanetricarboxylate (124-polymer).

In some examples of any of the preceding aspects/embodiments, the second polymer is 124-polymer with an inert polymer incorporated therein, the method further including leaching out the inert polymer after curing.

In some examples of any of the preceding aspects/embodiments, the method further includes forming micro-holes in the surface.

In some aspects, the present disclosure provides an apparatus for cultivation of cells. The apparatus includes a first chamber for cultivating cells. The apparatus also includes a mesh, supported in the first chamber, for cell cultivation thereon. The mesh includes a network of strands.

In some examples of any of the preceding aspects/embodiments, the first chamber has an opening defined therein to permit access to a second chamber. The mesh is positioned over the opening and has a porosity to enable at least partial access to the second chamber.

In some examples of any of the preceding aspects/embodiments, the porosity is about 40%.

In some examples of any of the preceding aspects/embodiments, the strands of the mesh each has a radius of curvature of about 5, 10 or 20 μm.

In some examples of any of the preceding aspects/embodiments, the mesh includes a regularly organized network of strands.

In some examples of any of the preceding aspects/embodiments, the mesh includes a randomly organized network of strands.

In some examples of any of the preceding aspects/embodiments, the mesh includes a micro-mesh.

In some examples of any of the preceding aspects/embodiments, the mesh provides a non-planar microtopology for cultivating cells.

In some examples of any of the preceding aspects/embodiments, each strand has an outer surface exhibiting convex microcurvature.

In some aspects, the present disclosure provides a method for cultivating cells. The method includes seeding podocytes on a cell cultivation surface at a seeding density. The method also includes introducing differentiation media to the podocytes, the differentiation media including all-trans-retinoic acid (ATRA), 1,25-dihydroxy vitamin D3 (Vit D3), and dexamethasone (Dex). The method also includes removing Dex from the differentiation media after a first time duration. The method also includes obtaining cultivated cells after a second time duration.

In some examples of any of the preceding aspects/embodiments, the cell cultivation surface exhibits at least one microcurvature providing a non-planar topology.

In some examples of any of the preceding aspects/embodiments, the at least one microcurvature is a convex microcurvature.

In some examples of any of the preceding aspects/embodiments, the at least one microcurvature is a concave microcurvature.

In some examples of any of the preceding aspects/embodiments, the surface has a porosity to enable at least partial communication between a first side of the surface and an opposing second side of the surface.

In some examples of any of the preceding aspects/embodiments, the porosity is about 40%.

In some examples of any of the preceding aspects/embodiments, the first side exhibits a first microcurvature and the second side exhibits a second microcurvature.

In some examples of any of the preceding aspects/embodiments, the first microcurvature is a convex microcurvature and the second microcurvature is a concave microcurvature.

In some examples of any of the preceding aspects/embodiments, the first side exhibits a convex microcurvature and the second side is substantially flat.

In some examples of any of the preceding aspects/embodiments, at least one micro-hole is defined in the surface.

In some examples of any of the preceding aspects/embodiments, the at least one micro-hole has a diameter in the range of about 0.4-10 μm.

In some examples of any of the preceding aspects/embodiments, the at least one microcurvature has an average diameter of about 20-100 μm and a height of about 5-20 μm.

In some examples of any of the preceding aspects/embodiments, the at least one microcurvature has a radius of curvature of about 5, 10, 50 or 20 μm.

In some examples of any of the preceding aspects/embodiments, the surface includes a plurality of convex microcurvatures.

In some examples of any of the preceding aspects/embodiments, the cell cultivation surface includes a mesh comprising a network of strands.

In some examples of any of the preceding aspects/embodiments, the strands of the mesh each has a radius of curvature of about 5, 10 or 20 μm.

In some examples of any of the preceding aspects/embodiments, the mesh includes a regularly organized network of strands.

In some examples of any of the preceding aspects/embodiments, the mesh includes a randomly organized network of strands.

In some examples of any of the preceding aspects/embodiments, the mesh includes a micromesh.

In some examples of any of the preceding aspects/embodiments, the mesh provides a non-planar microtopology for cultivating cells.

In some examples of any of the preceding aspects/embodiments, each strand has an outer surface exhibiting convex microcurvature.

In some examples of any of the preceding aspects/embodiments, ATRA is introduced at a concentration of 200 nM, Vit D3 is introduced at a concentration of 10 nM, and Dex is introduced at a concentration of 100 nM.

In some examples of any of the preceding aspects/embodiments, the seeding density is 50,000 cells/cm$^2$.

In some examples of any of the preceding aspects/embodiments, the first time duration is 2 days.

In some examples of any of the preceding aspects/embodiments, the second time duration is in the range of about 9 days to about 14 days.

BRIEF DESCRIPTION OF THE DRAWINGS

Reference will now be made, by way of example, to the accompanying drawings which show example embodiments of the present application, and in which:

FIGS. 1A and 1B show images of glomerulus and podocytes in vivo;

FIG. 1C shows an image of podocytes in a conventional 2D culture in vitro;

FIG. 2A is a diagram of an example Biowire™ strand platform;

FIG. 2B shows images of podocytes on a Biowire strand;

FIGS. 4A-4D are images illustrating the development of a cell culture device;

FIG. 4E shows an image of podocytes in vivo;

FIG. 7A shows immunostaining images for F-actin of differentiated podocytes cultivated under various conditions;

FIG. 7B shows immunostaining images for nephrin and WGA of differentiated podocytes cultivated under various conditions;

FIGS. 7C and 7D show 3-dimensional renderings of differentiated podocytes immunostained as in FIGS. 7A and 7B;

FIG. 8A shows immunostaining images for nephrin and WGA of differentiated podocytes on a microcurvature surface, with a series of zoomed-in confocal Z-slices;

FIG. 10A shows a podocyte plating, differentiation, and PAN stimulation protocol timeline for an example study;

FIG. 10B is a plot showing gene expression of differentiated podocytes with various PAN treatment conditions;

FIGS. 10C and 10D show immunostaining images for nephrin and WGA of differentiated podocytes treated without or with PAN;

FIG. 12FF is a plot comparing permeability of cells cultivated on different cultivation surfaces.

Similar reference numerals may have been used in different figures to denote similar components.

DESCRIPTION OF EXAMPLE EMBODIMENTS

Figure 2C:
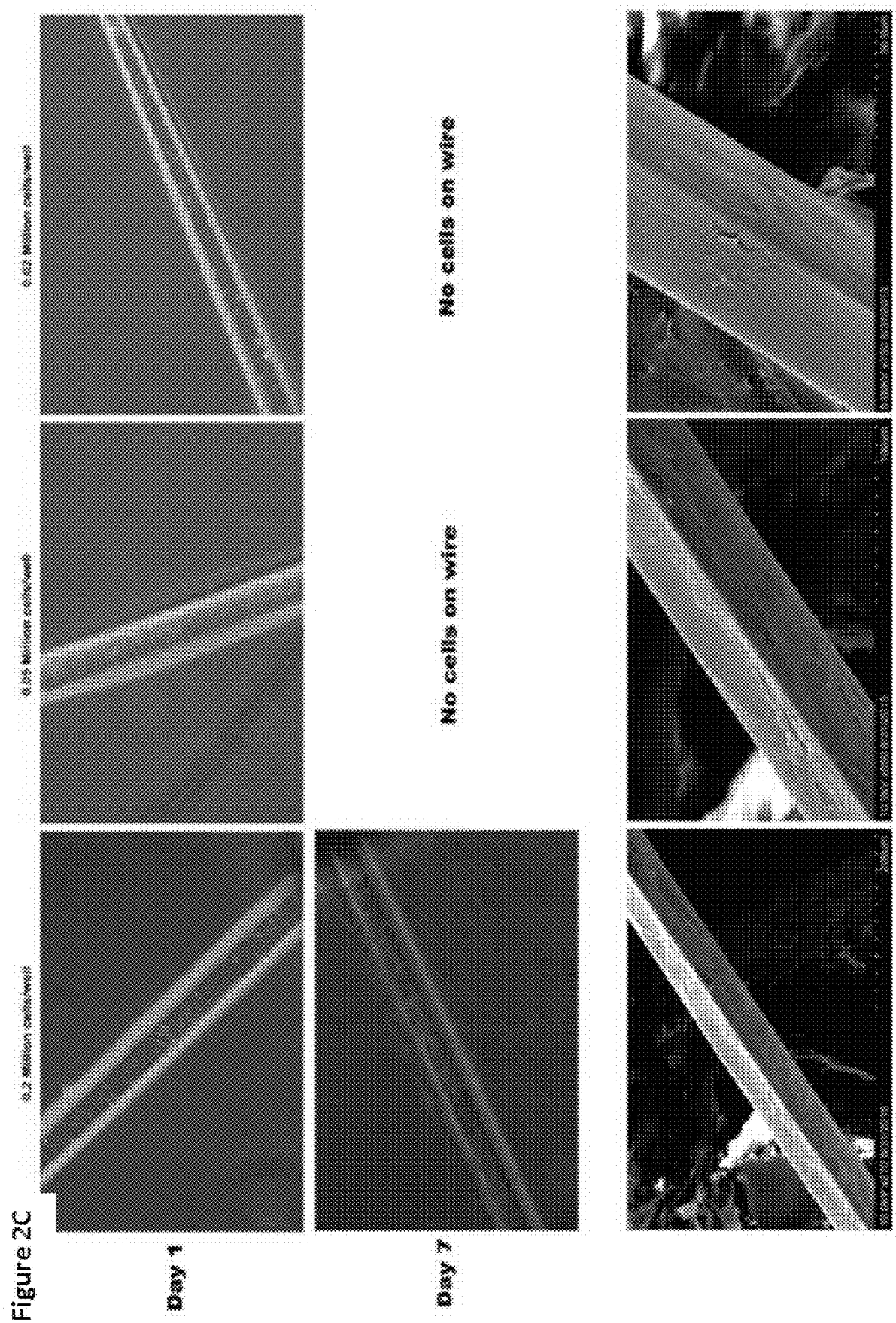
FIG. 2C shows images illustrating podocyte growth on a Biowire strand over seven days.

The methods and apparatus disclosed herein may enable more robust and consistent formation of morphological and/or functional features (e.g., slit diaphragms, foot process formation and interdigitation, among others) in podocyte cultures in vitro and measurements of permeability. The disclosed methods and apparatus may also be suitable to promote more physiological development of other cell types in vitro. Examples disclosed herein may enable greater control of cell microenvironment via topographical and biochemical cues that enable podocytes to achieve a physiological phenotype in vitro, as measured by the presence of slit diaphragm proteins, including nephrin, and the adoption of a morphological profile more redolent of in vivo podocytes.

Examples disclosed herein may be applicable for study of the kidney, and may help to improve kidney research by providing a biomimetic culture system that will enable podocytes to mature to more physiological extents. Culture of other cell types may also benefit from the present disclosure, which may help to improve study of other organs including, for example, the thymus, intestines, lungs and fat.

The native podocyte niche is characterized by spherically looping capillaries around which podocytes are intimately wrapped. Podocytes have an arborized morphology with interdigitated foot processes that wrap around the capillaries and connect to other podocytes. FIGS. 1A and 1B are images showing typical podocyte morphology in vivo, wrapped around a dense, curved cluster of glomerular capillaries with podocytes forming interdigitated processes.

The interdigitation of podocyte foot processes leads to a specific barrier function. It has been demonstrated that the slit diaphragm on these processes is the barrier structure for filtration in the glomerulus (11), and a hallmark of differentiation (9). This barrier function is critically dependent on the expression and appropriate structural maturation of key slit diaphragm proteins such as nephrin and podocin. These cells are being studied in vitro in an approach to better understand mechanisms of podocyte barrier function and the involvement in proteinuric diseases of the kidney (12). Many kidney diseases are associated with dedifferentiation/dysfunction of podocytes, where they lose the specialized features required for their function (13). Thus, the study of podocytes in vitro is currently concerned with understanding the cell's biology and the hallmarks of differentiation.

Conventionally, podocytes are cultured in vitro on flat, 2D culture plates or flasks. 2D culture may be done with conditionally immortalized cell lines, whereby cells are first cultured under growth-permissive conditions allowing immortalized podocytes to replicate (2). Then cultures are switched to conditions that encourage differentiation. This switchover to differentiation actuates marked changes in both morphology and gene expression. Cells phenotypically mature from cobblestone-like cells to arborized, flat, and spread out; and cells begin to express and evolve functional proteins typical of the slit diaphragm. Although immortalized cells lines are discussed in the present disclosure, it should be understood that the disclosed methods and apparatuses are not limited to use with immortalized cell lines. Other types of cells, including primary cells and stem cells, may be used with the methods and apparatuses disclosed herein.

Several techniques have previously been explored to culture podocytes with stable expression of key traits of differentiation. Co-cultures with glomerular endothelial cells (3, 4), chemical supplementation with vitamins and hormones (5-7), and careful temperature and overgrowth monitoring during culture (2, 8) have all become common practice in podocyte culture. However, while progress has been made in the study of podocytes, it has been difficult to reach appreciable levels of nephrin expression and slit diaphragm formation using the conditionally immortalized cell lines in the conventional 2D culture system, meaning that cultured cells remain relatively immature (2, 7, 9). In a conventional 2D culture, many of the hallmarks of podocyte differentiation, such as nephrin gene expression, reach plateaus that are far from the in vivo levels (8). FIG. 1C is an image showing an example in vitro 2D culture of podocytes, showing minimal arborisation and interdigitation of processes, compared to podocytes in vivo (see FIGS. 1A and 1B).

The present disclosure presents example biomimetic techniques that may help to overcome or raise this plateau of the culture system to achieve more useful, higher-fidelity levels that better match in vivo maturity. In some examples, the present disclosure describes a cell culture apparatus that may be provided using microfabrication techniques.

Microfabrication is a useful tool for tissue engineering because cells are responsive to microscale physical cues (14). For example, making unidirectional grooves or channels has been demonstrated to help in the alignment of cardiac cells (15, 16), for the formation of microvasculature (17), or for designing direction-specific mechanical properties within a scaffold or engineered tissue (18-20). Microfabrication is frequently used for building organ-on-a-chip systems (21, 22). However, the standard approach using optical patterning on an SU-8 polymer typically produces straight-angled features. Such straight-angled features may be less representative of in vivo structures that are rounded and not angular in nature.

Several approaches have been devised to enable generation of curved features in the micro scale including, for example: application of selective layer-by-layer UV-curing of photoresist to create arrays of cone-like features (23), using thin polydimethylsiloxane (PDMS) membranes with applied vacuum to generate curved channels (24, 25), employing textile technology to fabricate wavy micropatterns (26), or the use of reflowing polymers which melt around edges at certain temperatures (43). Similarly, thin glass rods have also been used as alternates to channels for studying cell migration on the curved rod (27). However, labour-intensive or multi-step fabrication techniques, with limited flexibility in control over feature specifics, may be less amenable for scaling up to high-throughput applications.

In examples disclosed herein, a microfabrication technique is described that uses glass beads as a template to incorporate curvature of a specifically defined radius into a master mold (which may be referred to herein as a "bubble" surface), suitable for use in form of an apparatus for podocyte culture. By adding biomimetic 3D micro-hemispheres into the culture platform, the cells are presented with a unique type of stimulus, that of convex curvature, to respond to during their differentiation process. As demonstrated by example studies described below, it was found that such a curved surface in the culture apparatus resulted in enhancement of nephrin gene expression, nephrin protein localization, and arborizing morphology. It is expected that cells cultivated in such an apparatus may also exhibit more physiological nuclear shape, cell stiffness and membrane fluidity, and show similar responses to other types of curvature as well (e.g. concave).

In the glomerulus in vivo, the podocyte experiences out-of-plane curvature. The example apparatuses disclosed herein may provide topography that approximates or mimics the curving glomerular capillary structures found in vivo. Such a biomimetic structure may provide a physical stimulus that promotes podocyte differentiation in vitro, leading to more appreciable levels of nephrin gene expression. The example microfabrication technique disclosed herein may enable micro-curvature features to be incorporated into a cell culture apparatus and further may be amenable to high-throughput applications.

Development of a podocyte culture apparatus with curvature began with a Biowire™ strand setup, inspired by a single capillary. FIG. 2A is a diagram illustrating how podocytes wrap around a capillary in vivo. As shown, three individual podocytes 202 are wrapped around a single capillary 204. The podocytes 202 form filtration slits 206 over the capillary 204. A Biowire strand may refer to a strand of material, such as a hollow microscale tube, which may be made from biocompatible elastomeric polymers with tissue-like mechanical properties. Thus, Biowire strands may act as a synthetic version of a tubular blood vessel or capillary. The outer surface around a Biowire strand may provide a surface with non-planar microtopology, which may be amenable to cultivation of podocytes. In the present disclosure, a non-planar microtopology refers to a surface with non-flat features on a micron scale. The tubular blood vessel-like structures were explored for cell culture with Biowire strand and mesh setups. FIG. 2B shows example images of Biowire strands coated with Matrigel™ to facilitate podocyte attachment after seeding via gravity-assisted cell settlement from single-cell suspension solutions. FIG. 2C shows images of example seeded Biowire strands, seeded at different initial densities, at day 1 and day 7 of cultivation. Cell suspension density of 0.2 million cells/well was found to be a suitable cell seeding density to ensure cell attachment onto the Biowire strand while avoiding over-confluence. Close-up images of the Biowire strand at day 7, seeded at an initial density of 0.2 million cells/well, are shown at the bottom of FIG. 2C.

Figure 3:
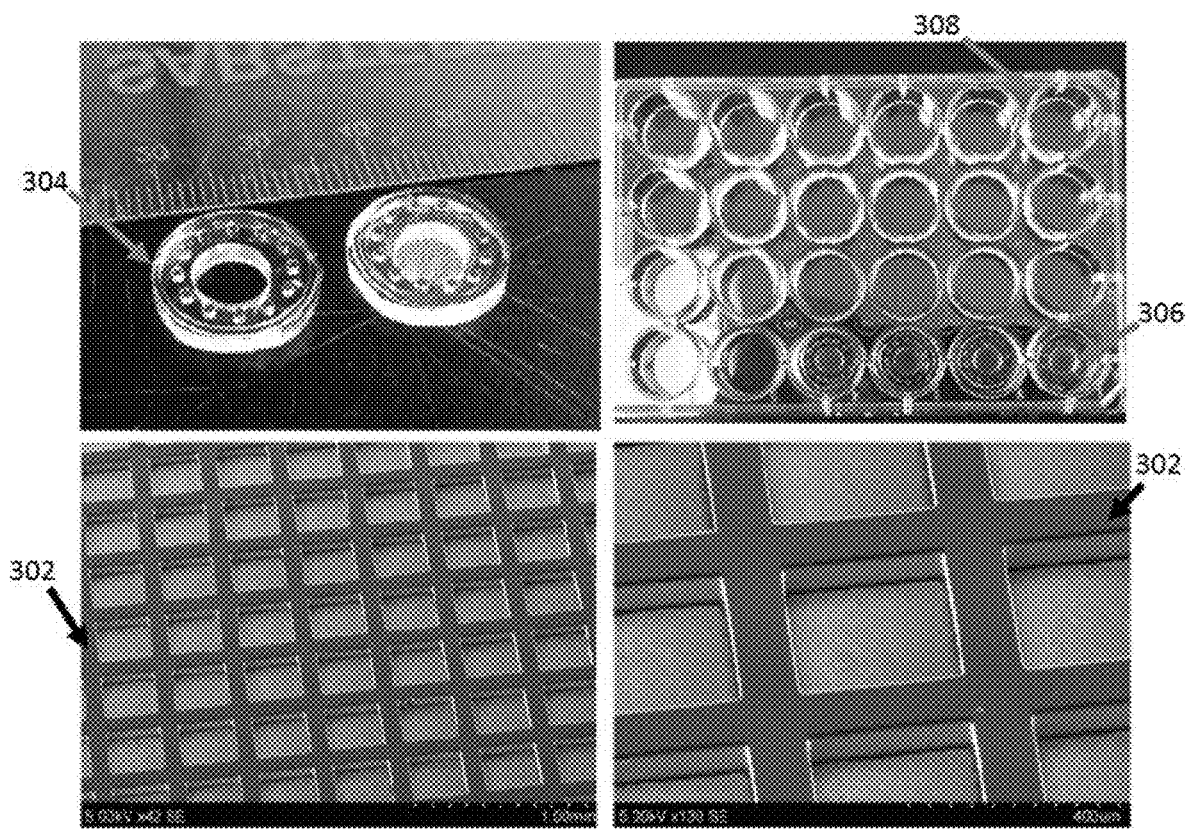
FIG. 3 shows images of an example mesh system.

The single wire setup was found to have an unacceptably low cell capture efficiency during seeding, resulting in cell waste and very little useful content per well. In a further development, a mesh system was created for cultivating cells. A mesh system may be conceptually similar to a network of strands or network of Biowire strands. In the example discussed below, the mesh is a regularly organized network of strands, however in other examples the mesh may be a randomly organized network of strands. FIG. 3 is an example image showing a mesh system. In the example shown, the mesh system includes a micro-mesh 302. A micro-mesh 302 may refer to a mesh 302 having micron-scale dimensions. The strands in the mesh 302 provide outer surfaces that exhibit a non-planar microtopology (e.g., convex microcurvature), which may be amenable to cultivation of podocytes. The mesh 302 may be supported by a holder 304 to suspend the mesh in a well 306 of a well plate 308.

The mesh structure was found to increase the surface area for podocyte culture on the 3D wire-like configuration, enabling a higher cell capture efficiency per well, and higher working volumes for subsequent analyses.

A Biowire strand may represent a single capillary structure, and a mesh system may thus represent a network of capillaries. However, the native environment of podocytes in the glomerulus does not consist of single capillaries or even a network of straight capillaries, but rather of a dense bed of looped capillaries. Although the mesh system provided cell cultivation that may be suitable for some applications, a cultivation platform with more non-planar microfeatures, such as microcurvatures, may provide better results.

Thus, the next development of the cell cultivation apparatus was to include the presence of intense curvature in the apparatus. FIGS. 4A to 4D illustrate the development of the cell cultivation apparatus from a single Biowire strand having an outer surface with non-planar microtopology (FIG. 4A) to a mesh structure where the strands of the mesh each have an outer surface exhibiting non-planar microtopology (FIG. 4B) to a mesh with additional protrusions exhibiting convex microcurvatures (FIG. 4C) and a surface with protrusions exhibiting convex microcurvatures (FIG. 4D). In these various example structures, the non-planar microtopology mimics the curvature of the in vivo glomerular capillary bundles (shown in FIG. 4E). The convex microcurvatures in the microtopology of FIG. 4D is similar to the 3D structural microfeatures of the cell's in vivo microenvironment. It has also been found that the example microtopology apparatus is compatible with bulk culture and higher-throughput system evaluation techniques.

Figure 5A:
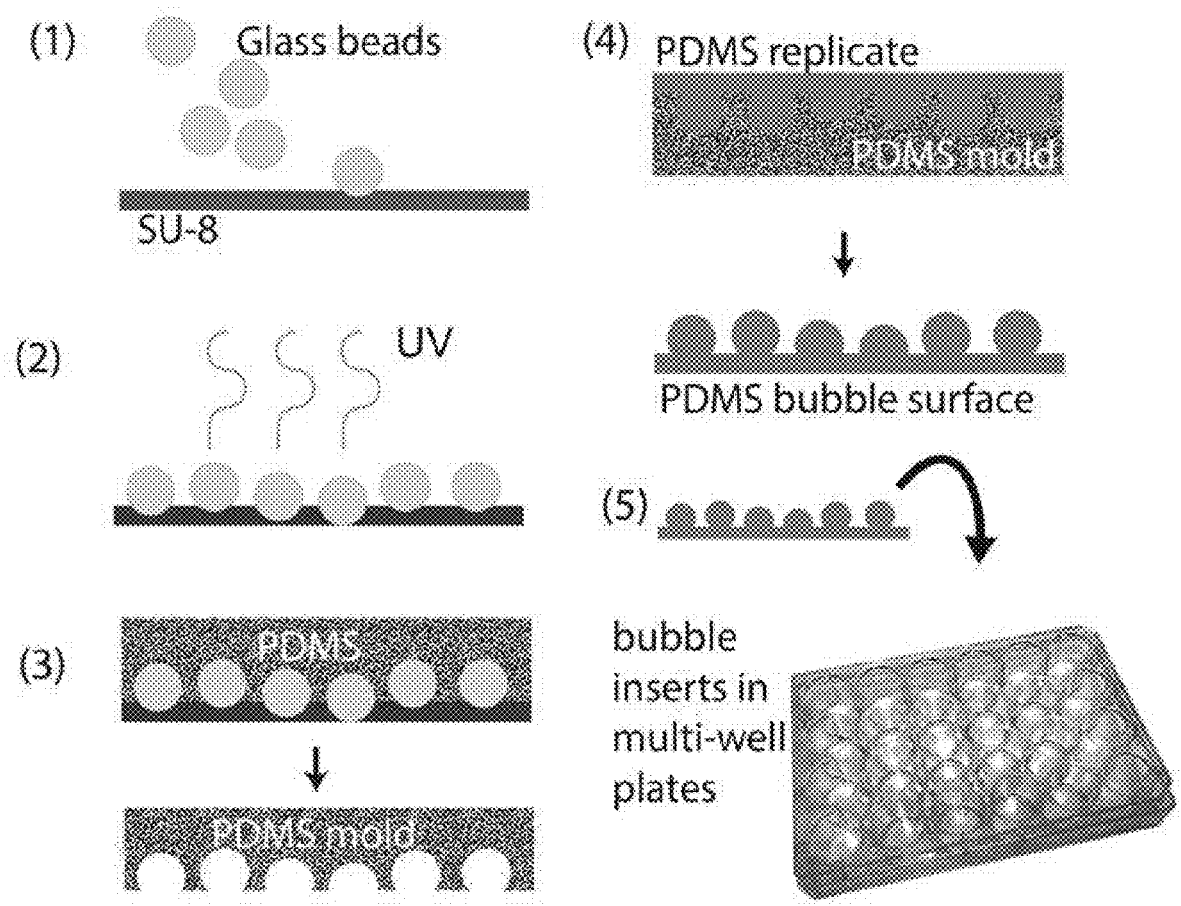
FIG. 5A illustrates an example method for fabricating an example cell cultivation system having convex microcurvatures.

An example technique for fabrication of the microtopology apparatus is now described. FIG. 5A illustrates an example method for fabrication of an example apparatus for cultivation of cells, exhibiting non-planar microtopology. In this example, the features exhibiting non-planar microtopology are convex microcurvatures provided by partially-spherical protrusions, each protrusion providing a convex microcurvature.

At 1), glass beads 502 were poured onto a substrate 504, such as a silicon wafer spin-coated with SU-8 2050 (e.g., about 50 µm thick), covering the surface with glass beads. Although glass was used in the material in this example, other materials may also be suitable.

In this example, the glass beads 502 were all of a similar diameter (in this case, approximately <100 µm, G4649 Sigma-Aldrich). In other examples, the glass beads 502 may be of varying diameters. The glass beads 502 may have diameters in the range of about 10-1000 µm, for example. The beads 502 may be arranged in an organized fashion (e.g., close-packed, or self-assembling array) or in a random fashion. Where the glass beads 502 are of different diameters, arrangement of the glass beads 502 on the wafer 504 may be size-dependent.

At 2), the bead-covered surface was exposed to UV irradiation, thereby fixing the glass beads 502 together with the SU-8 onto the wafer 504.

At 3), the bead-covered surface was then used to create an inverse mold 506 with concave curvatures by curing a polymer over the bead-covered surface. In this example, PDMS was used to form the inverse mold. Other materials may also be suitable. For more robustness and/or ease of handing, the inverse mold 506 may be bonded to another silicon wafer (not shown). For example, the inverse mold 506 may be plasma bonded to another silicon wafer, and fully cured at 120° C. The inverse mold 506 may thus serve as the master mold to fabricate a surface exhibiting convex microcurvatures.

At 4), a microcurvature surface 508 with out-of-plane convex microcurvatures (also referred to as "bubbles") was formed by curing a polymer (e.g., PDMS or poly(octamethylene maleate (anhydride) 1,2,4-butanetricarboxylate (commonly referred to as "124-polymer")) using the master mold 506. Although PDMS was used in this example, other suitable materials may also be used.

At 5), the microcurvature surface 508 is used in a cell culture device, such as a multi-well cell plate 510. For example, in order for the microcurvature surface 508 to be used in the wells of a cell culture plate 510, portions of the surface 508 may be cut and fitted into individual wells 512. In this example, circular portions were punched out from the microcurvature surface 508, autoclaved or otherwise sterilized, and then placed as inserts into individual wells 512 of a 24-well plate 510. The result is an apparatus for cell cultivation that provides a surface with microcurvature features.

The resulting apparatus includes a chamber for cultivating cells, provided in this example by a well 513 of the well plate 510. The microcurvature surface 508 is supported in the chamber. Although described above as a surface having convex microcurvatures formed as "bubble" structures, in some examples the non-planar microtopology may be provided by any non-planar microfeature, for example the outside surface of a mesh or Biowire strand structure, as described above with reference to FIGS. 4A-4C. Various examples and studies are described with reference to a surface with convex microcurvatures, however it should be understood that similar benefits and effects may be achieved using an apparatus with other non-planar microtopology, including concave microcurvatures, and strand or mesh structures.

The example method described above is relatively simple and introduces significant curvature effects into the cell environment, for a more biomimetic and geometric 3D cell culture.

The dimensions (including height, diameter, and coverage of the curvatures on the microcurvature surface) of an example microcurvature were investigated using a profilometer (KLA-Tencor P16+ Surface Profilometer at the Ontario Centre for the Characterisation of Advanced Materials, University of Toronto, Canada). Multiple cross-sectional profiles at fixed separations were measured, leading to the mapping of a 3D surface. Five 400 by 400 µm squares from three PDMS inserts were profiled with an optimized resolution of 4 data points per µm in the x-axis and 1 data point per µm in the y-axis.

The reconstructed 3D profile maps were analysed in ImageJ using the Analyze Particles feature. This analysis provided the diameter of each curvature feature (i.e., a single "bubble"), as well as the percent area that was covered by curvatures. In addition, the maximum grey value per curvature was measured, which was used to calculate each curvature's height by correlating it to the grey values of the elevation scale bar (produced by the profilometer).

Figure 5B:
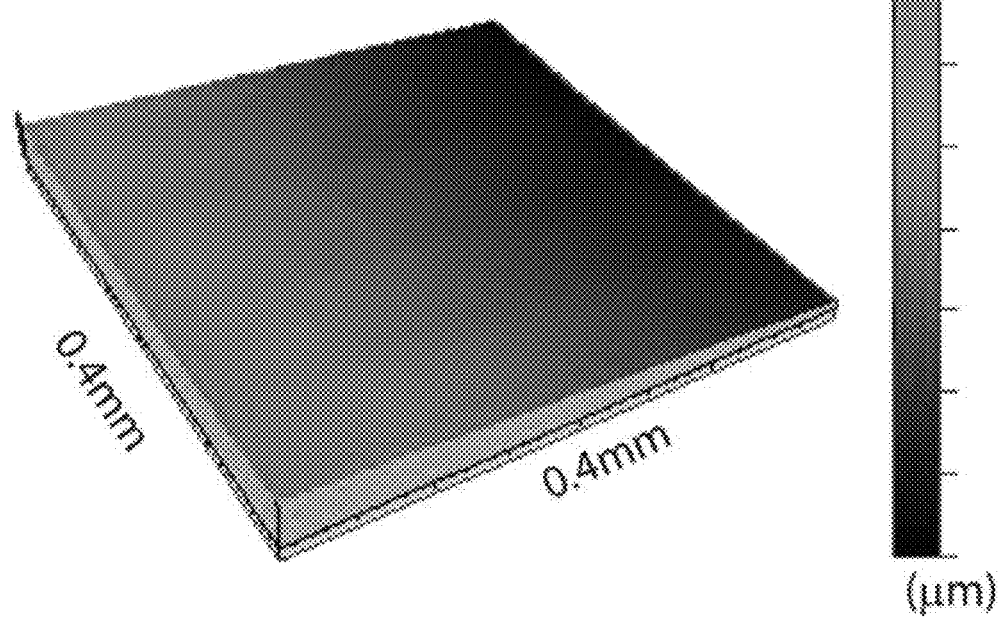
FIGS. 5B and 5C show profilometer 3D re-constructions of a flat surface and an example microcurvature surface.
Figure 5C:
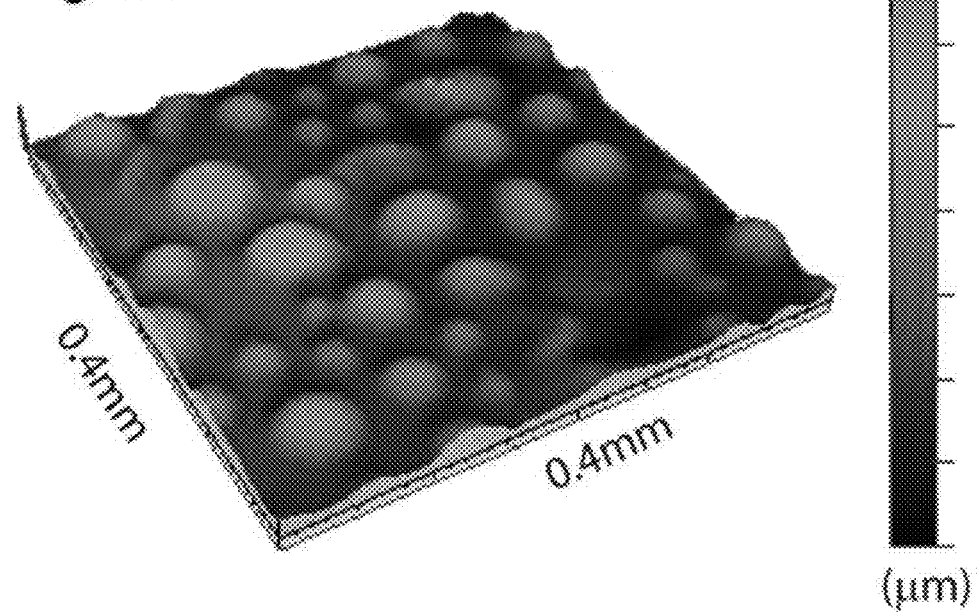
Figure 5D:
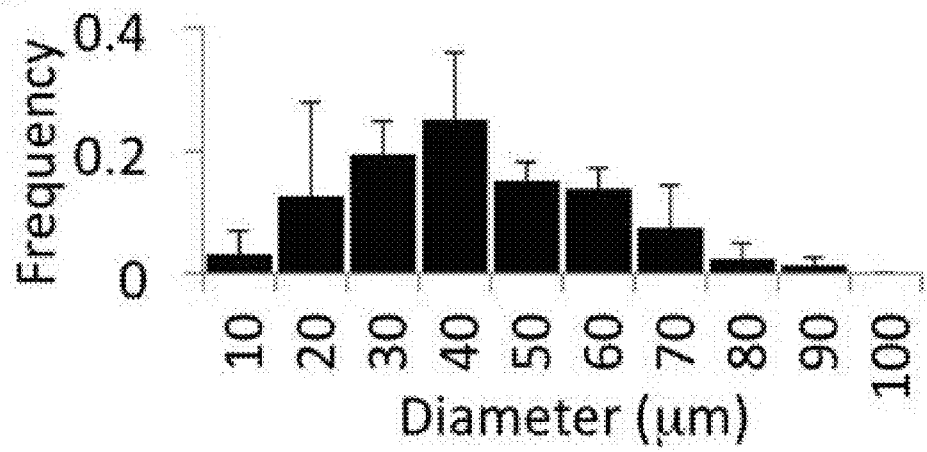
FIG. 5D is a histogram plot of the microcurvature diameter distribution.
Figure 5E:
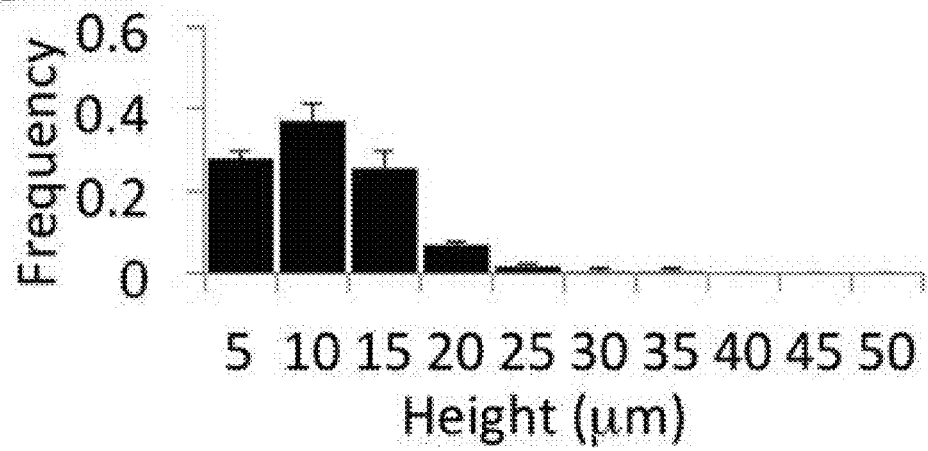
FIG. 5E is a histogram plot of the microcurvature height distribution.

FIG. 5C is a profilometer mapping of an example microcurvature surface. As shown in FIG. 5C, the surface fabricated in accordance with the present disclosure shows significant out-of-plane hemispherical features. By contrast, profilometer mapping of a flat surface is shown in FIG. 5B, showing the flat surface is free of significant topography. Profilometry of the bubble surface confirmed the average dimensions of the microcurvature introduced in the platform. In the example microcurvature surface in which glass beads of about 100 µm were used to fabricate the master mold as described above, the average exposed hemisphere from the microcurvature surface has a diameter of 40.5±6.2 µm with a height of 7.8±0.1 µm, covering 38.3±7.7% of the platform surface, and the variation in the diameter and height within an area is shown in histograms in FIGS. 5D and 5E. This spectrum of diameters and heights is sufficient to cover the full range of dimensions from small blood vessels (typically about 20-100 µm in diameter) to capillaries (typically about 5-20 µm in diameter) (30). It should be understood that the microcurvatures are not limited to the dimensions described above. For example, microcurvatures of different diameters and heights may be achieved by using different sizes of glass beads for fabrication. For example, a surface may be fabricated to contain microcurvatures having diameters in the range of about 20-100 µm, and having heights in the range of about 5-20 µm, or other dimensions depending on desired application. In some examples, a single microcurvature surface may be fabricated to contain microcurvatures of different dimensions (e.g., by using a mixture of differently sized glass beads using fabrication).

In some examples, a biochemical stimulation regimen may be used with the disclosed cell cultivation apparatus. The following is a description of a study that was carried out to investigate a suitable protocol for cultivating cells. The different biochemical stimulation described below may be used together with the disclosed apparatus for cell cultivation, including any variation of the cultivation surface described above, or may be used separately from the disclosed apparatus. Similarly, the disclosed apparatus may be used separately from the biochemical stimulation protocol.

In the study described below, cultivation parameters that were studied include: seeding density; culture media; incubation temperatures; introduction of toxins; as well as presence of microcurvatures on the cultivation surface.

The seeding density was assessed because it is a key parameter in podocyte differentiation (2). Podocytes are highly sensitive to overgrowth. Overgrowth due to an overly high seeding density could lead to a loss of ability to differentiate (2). Thus, cultivation was performed at low- and high-density seeding conditions (15,000 cells/cm$^2$ and 50,000 cells/cm$^2$, respectively) to investigate the range of applicability of the microcurvature surface for podocyte differentiation.

Figure 6A:
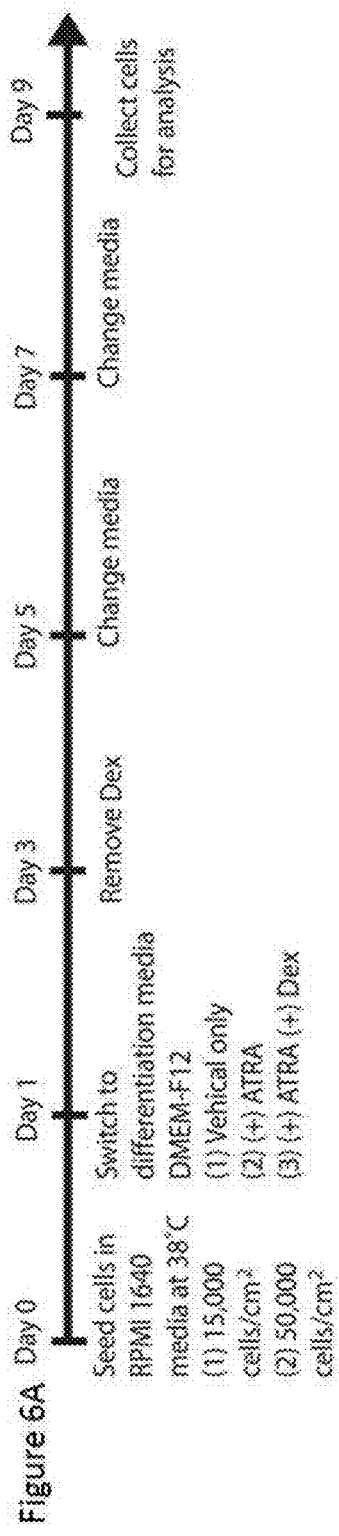
FIG. 6A is a podocyte plating and differentiation protocol timeline for an example study.

The culture conditions were also investigated by considering different culture media and incubation temperatures. The conditionally immortalized podocyte cell lines are temperature-sensitive and will undergo different cell cycles depending on the temperature of incubation (9). The assessment of culture conditions compared use of RPMI 1640 versus DMEM-F12 basal media; hormonal supplementation with 1,25-dihydroxyvitamin D3, all-trans-retinoic acid, and dexamethasone; and a differentiation temperature of 37° C. and 38° C. (6, 7, 9). Ultimately, three media conditions were used at 38° C. for successive experiments: (+)ATRA, (+)ATRA(+)Dex, and vehicle-only control. ATRA may have a concentration in the range of about 100 nM-10 µM, DEX may have a concentration in the range of about ≤100 nM, and Vit D3 may have a concentration in the range of about 100 nM-10 µM. FIG. 6A shows the podocyte plating and differential protocol timeline used in this investigation.

Unless otherwise stated, all cell culture materials were obtained from Thermo Fisher Scientific, USA. E11 murine podocytes are a conditionally immortalized cell line, and are grown under different conditions to encourage the proliferative versus differentiating stages. Cells were first grown under conditions permissive to proliferation before seeding for the differentiation step. In the example described below, the cells were proliferated and then collected and seeded on the cultivation surface for differentiation. In other examples, the cells may be seeded on the cultivation surface and allowed to proliferate on the surface for several days before conditions are changed to promote differentiation.

In this example study, the podocytes were plated on a collagen I coated T175 flask in growth media: RPMI 1640 media containing GlutaMAX and HEPES, with added 10% (v/v) fetal bovine serum (FBS), 1% (v/v) penicillin-streptomycin (P/S), and supplemented with 10 units/mL recombinant murine interferon gamma. Podocytes were grown at 33° C. until roughly 80% confluent. Then podocytes were trypsinized and collected for seeding in differentiation conditions. Prior to seeding, the microcurvature inserts were coated with Matrigel™ (1:60 dilution from 9.3 mg/mL stock solution) for 2 hours.

On day 0, cells were seeded with growth media at low or high seeding density (15,000 cells/cm$^2$ or 50,000 cells/cm$^2$, respectively) on either a microcurvature surface or a flat surface (in the 24-well plate described above) and transferred to 38° C. to begin differentiation. Cells were allowed to attach for one day, and then on day 1 the culture media was changed to supplemented media: DMEM-F12 basal media (Life Technologies, USA) containing 10% (v/v) FBS, 1% (v/v) P/S, and select biochemical supplementation.

As discussed above, three media groups were compared: (1) (+)All-trans-Retinoic acid (ATRA, Sigma-Aldrich), (2) (+)ATRA(+)Dexamethasone (Dex, Sigma-Aldrich), and (3) vehicle only control. The (+)ATRA group consisted of DMEM-F12 basal media and 10 nM 1,25-dihydroxyvitamin D3 (Vit D3, Enzo Life Sciences, USA) and 200 nM ATRA. The (+)ATRA(+)Dex group was identical to the (+)ATRA group but had an additional 100 nM Dex included for the first 48 hours of supplemented culture, with its use discontinued on day 3 of the culture process. The vehicle-only control included no supplements. Media was changed every other day until day 9 when cells were either harvested for RNA isolation and gene expression analysis, or fixed for imaging. In other examples, the cells may be cultivated for a longer period of time, for example cells may be cultivated until day 14 according to cell line protocol. FIG. 6A illustrates the podocyte plating and differentiation protocol timeline described above.

On day 9, cells were washed with warm, non-supplemented RPMI 1640 basal media prior to lysing and RNA isolation. A High Pure RNA Isolation Kit (Roche) was used according to manufacturer's instructions, using 50 µL of elution buffer for the final step. Each sample from the study consisted of 3 individual wells pooled together, to ensure that a sufficient amount of RNA was being collected. Thus, 9 wells were seeded for each group to generate n=3 samples per condition. Isolated RNA was converted to complementary DNA (cDNA) using the High Capacity cDNA Reverse Transcription Kit (Applied Biosystems, USA) for ensuing PCR applications. RNA solutions were diluted to a final 7.5 ng/µL in a total reaction volume of 60 µL. Real-time PCR was run on the generated cDNA using the TaqMan Gene Expression Assay (Applied Biosystems). cDNA was diluted to 3.33 ng/µL in a volume of 9 µL, for a total of 30 ng cDNA per reaction. Taqman assays were run on a qPCR Lightcycler 480 (Roche, Switzerland) according to the following PCR conditions: incubation at 95° C. for 10 min, 55 cycles of 95° C. for 15 sec, 60° C. for 1 min, and 72° C. for 1 sec. Expression of murine nephrin gene (NPHS1, Thermo Fisher Scientific) and the housekeeping gene Beta-2-Microglobulin (B2M, Thermo Fisher Scientific) was determined using relative quantification analysis (28), where C57/bl6 mouse whole kidney cDNA was used as a positive control and as a normalizer in calculations.

For immunofluorescent staining, cells were first washed with Dulbecco's phosphate buffered saline (DPBS, Life Technologies) and then fixed in 4% paraformaldehyde solution for 15 min at room temperature, followed by another wash with DPBS. For F-actin staining, the cells were permeated and blocked in 10% (v/v) FBS and 0.25% Triton X100 in DPBS for 1 hour. Next, the cells were incubated with Alexa Fluor® 660 phalloidin (Thermo Fisher Scientific) for 1 hour. For Nephrin and Wheat Germ Agglutinin (WGA) staining, the cells were blocked in 10% normal goat serum for 1 hour. Next, the cells were incubated in primary anti-Nephrin antibody (Thermo Fisher Scientific) overnight at 4° C. followed by incubation with FITC goat anti-rabbit IgG (1:200 dilutions, Abcam, UK) for 1 hour at room temperature. Lastly, the cells were incubated with Rhodamine-WGA (1:1000 dilution, Vector Laboratories, USA) for 10 min at room temperature.

Fixed cells were dehydrated in the 24-well plates in a serial ethanol wash over a course of 2 hours, in five steps going from 25% to 100% ethanol in DPBS. After ethanol dehydration, the PDMS platform inserts with cells were removed from their wells and sliced into quarters in order to fit size constraints for critical point drying. The samples were then dried at the critical point, and sputter-coated with gold before scanning electron microscopy (SEM) imaging on a Hitachi S-3400N Scanning Electron Microscope.

To analyze the results, normality and equality of variance were tested using SigmaPlot 12. Two-way ANOVA followed by pairwise comparisons with Fisher LSD method were used to determine the statistical significance and assess the interactive effects of factors in FIGS. 6B and 6C.

Figure 6B:
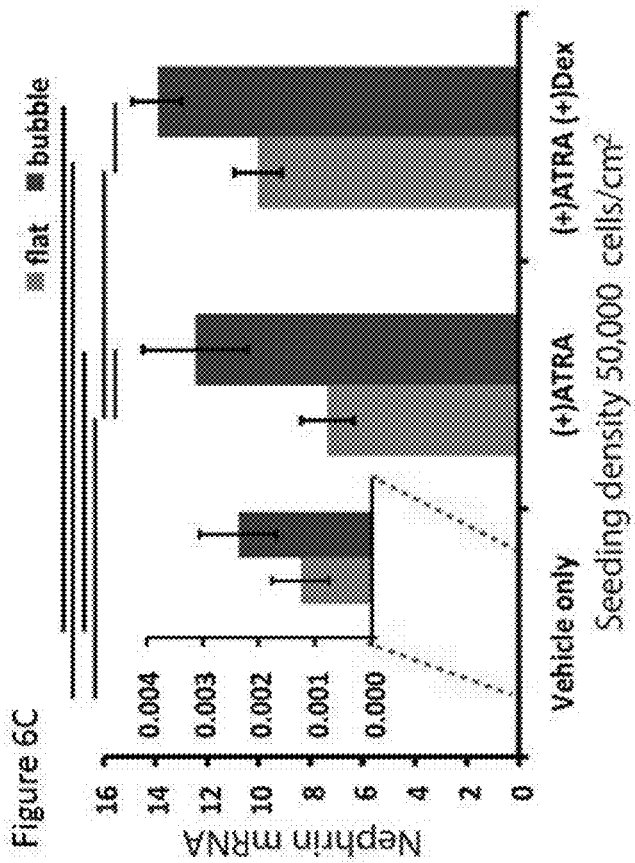
FIGS. 6B and 6C are plots showing gene expression of differentiated podocytes cultivated under various conditions.
Figure 6C:
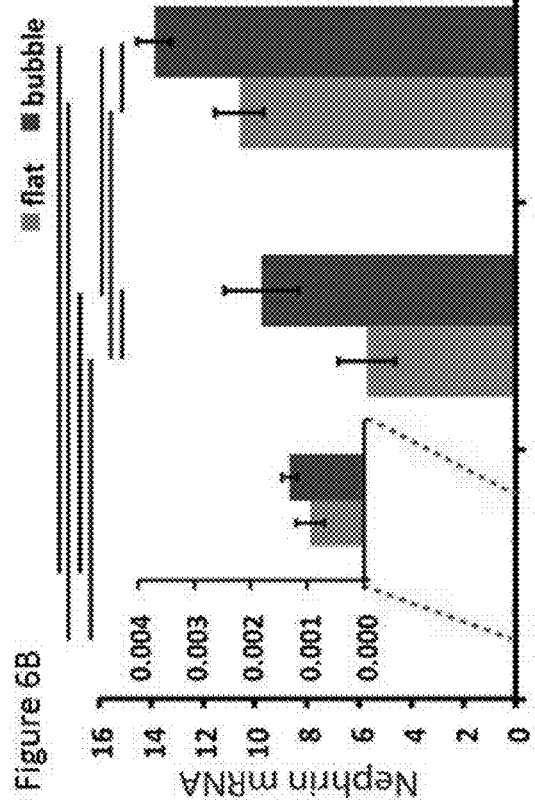

FIG. 6B shows gene expression results from RT-qPCR of differentiated podocytes under various conditions on day 9 at initial cell seeding density of 15,000 cell/cm$^2$ (average±s.d., n=3). Lines indicate significant difference between groups with $p<0.05$. The table shows detailed statistical analysis on the data set. FIG. 6C shows gene expression results from RT-qPCR of differentiated podocytes under various conditions on day 9 at initial cell seeding density of 50,000 cell/cm$^2$ (average±s.d., n=3). Lines indicate significant difference between groups with $p<0.05$. The table shows detailed statistical analysis on the data set.

After 9 days of differentiation, the results demonstrated that, in all culture conditions, cultivation using the microcurvature surface consistently yielded cells with greater upregulation of nephrin gene (NPHS1) than cultivation using the flat platform (see results in FIGS. 6B and 6C), and as compared to the undifferentiated groups. An upward trend was observed in cultures with non-supplemented culture media (i.e., vehicle-only control), but it was more pronounced where cells were cultured with ATRA and Dex supplement. It was found that the presence of ATRA and Dex significantly enhanced nephrin gene expression by about 4 orders of magnitude as compared to the vehicle control, while surface curvature further augmented nephrin upregulation. The cell seeding density was not found to alter the effects of either topographical or biochemical cues. It should be noted that the expression results generated are normalized to mouse whole kidney cDNA, thus the magnitude of upregulation is compared to the heterogeneous kidney sample and not the expression of a pure native podocyte population. An interaction effect was also observed, whereby topography and biochemical stimulation acted in a cumulative fashion.

Accordingly, based on the results of this example study, a method of cultivating cells may be proposed, in which the cells are cultured with ATRA, vitamin D, and Dex supplement. Such biochemical cues may be beneficial for cultivation of cells, in particular podocytes, even without the use of the microcurvature surface.

Phenotype improvements were also observed with topography and biochemical stimulation. Immunofluorescent staining of differentiated podocytes on day 9 showed differences in cell morphology between the vehicle-only control group and the supplemented groups, as well as between the groups cultivated using the microcurvature surface and the flat platform.

Cells in the vehicle-only control group showed elongated morphology while the cells in the (+)ATRA and (+)ATRA (+)Dex groups showed radial spreading and larger surface areas for the formation of cell-cell contact points between multiple cells. F-actin staining revealed the structure of intracellular microfilaments extending to the cell-cell boundary, and structurally supporting rudimentary protrusions. FIG. 7A shows immunostaining for F-actin of differentiated podocytes in different conditions on day 9 (scale bar represents 30 µm for images in rows 1 and 3, and 10 µm for images in rows 2 and 4). FIG. 7B shows immunostaining for nephrin and WGA of differentiated podocytes in different conditions on day 9 (scale bar represents 100 µm for images on rows 1 and 3 and 50 µm for images in rows 2 and 4). The additional influence of the microcurvature topography is shown by the change from compacted, spindle-like cells to arborized morphologies. This was especially evident in the vehicle-only group.

From the confocal cross-section of the podocyte cell layer on the microcurvature surface, it was found that cell nuclei/ bodies were positioned in between and at the bottom of microcurvature structures while the cell periphery and processes extended out onto the microcurvature tops. FIGS. 7C and 7D show 3D renderings of differentiated podocytes immunostained for F-actin (FIG. 7C) or nephrin and WGA (FIG. 7D) on day 9. FIG. 8A shows an example immunostaining image for nephirn and WGA of differentiated podocytes under media condition (+)ATRA (+)Dex on day 9, with a series of zoomed-in confocal Z-slices. Slices are ordered from top to bottom of the microcurvature surface. Distance between the slices is 2 µm (scale bar represents 100 µm (large) and 25 µm (zoom-in)).

In a number of samples, multiple cells with distorted nuclei were observed circling around a microcurvature at the valleys between microcurvatures, while their cell periphery and processes met and formed dense, mesh-like junctions with neighbouring cells on top of the microcurvature. This behaviour is similar to how podocytes use their foot processes to wrap around capillaries in vivo.

Figure 8B:
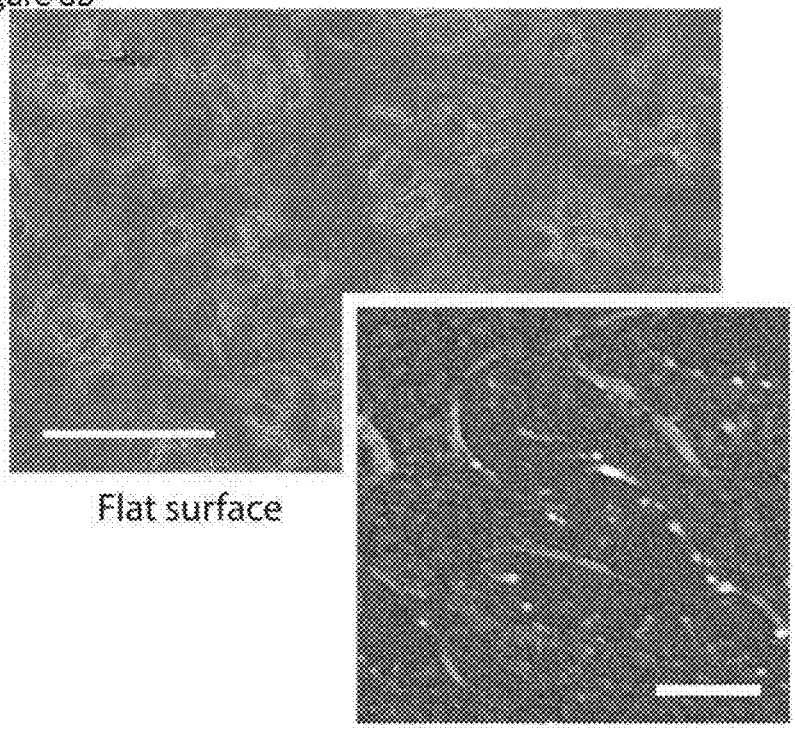
FIGS. 8B and 8C show SEM images of foot processes from differentiated podocytes cultivated on flat and microcurvature surfaces.
Figure 8C:
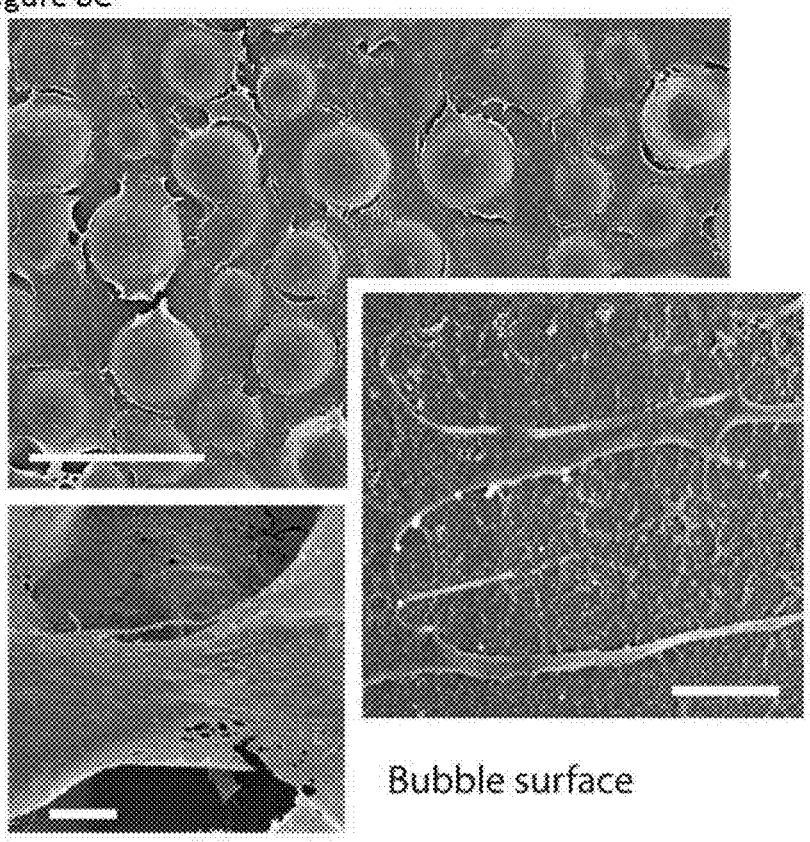

In addition, using SEM, scaling protrusions and evidence of foot process formation could be observed. FIGS. 8B and 8C show example SEM images of foot processes from differentiated podocytes on the flat and microcurvature surfaces under the same treatment group as in FIG. 8A (scale bar represents 100 µm, right side insets scale bar represents 2 µm, and scale bar in left side inset in FIG. 8C represents 5 µm). The cells on microcurvature platforms formed contact points between microcurvatures and other cells, as well as suspended protrusions (see FIGS. 8A and 8C). The microcurvature topography effectively induced this suspended behaviour, which is not possible to recapitulate on the flat surface.

To further illustrate the junctions between the cells, the cells were stained for nephrin and the cell membrane labeled with WGA (see FIGS. 7B and 7D). Nephrin proteins were found consistently localized on top of the microcurvature structures (see FIGS. 7B, 7D and 8A) whereas on the flat surface they were diffused throughout the entire cell, with some distribution at the inter-cellular junctions in the (+)ATRA (+)Dex group. Undifferentiated samples (day 0) showed minimal or no nephrin staining, and no apparent localization patterns (see FIG. 7B). In fact, the microcurvature-induced localization of nephrin was so consistent that localized nephrin expression was observed on top of the microcurvature structures even in the vehicle-only control group, whereas in the flat counterpart the nephrin expression was diffused throughout the whole cell. On the flat surface the localization of nephrin to the cell boundary was realized only with ATRA and Dex supplementation, but was easily induced under all conditions on the microcurvature surface.

Figure 9A:
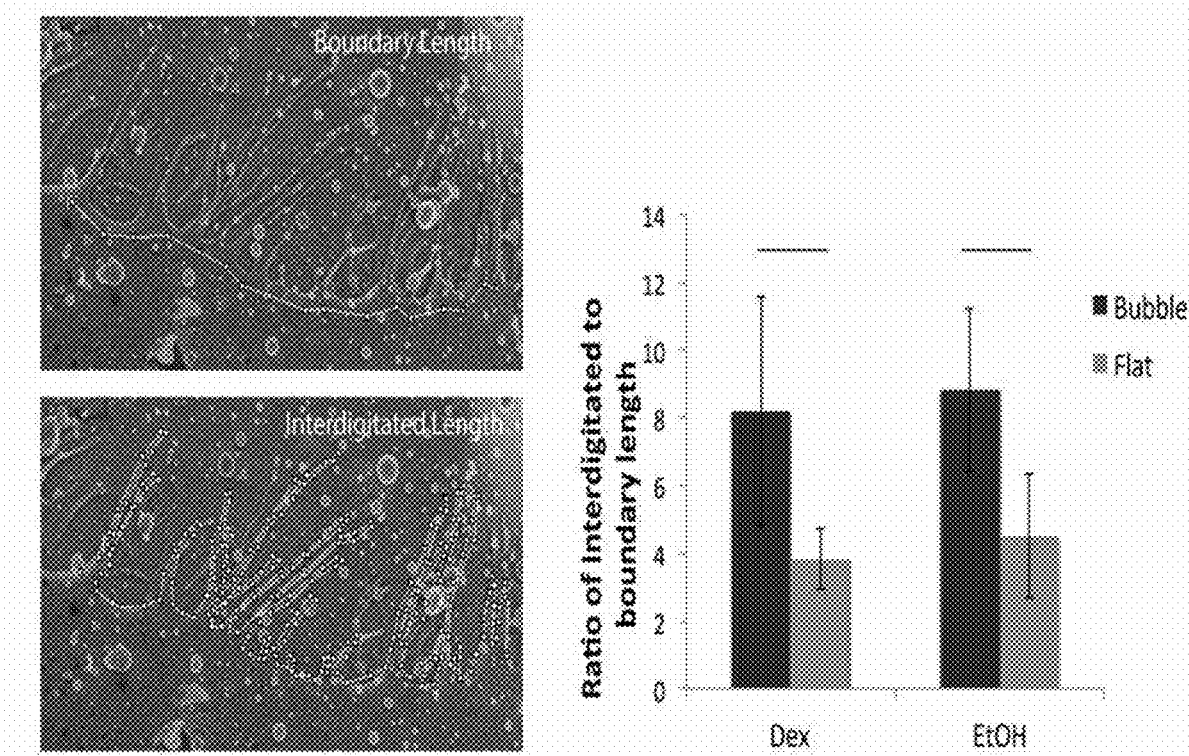
FIG. 9A shows a plot and images comparing nuclei aspect ratios of cells cultivated on a flat surface and cells cultivated on a microcurvature surface.
Figure 9B:
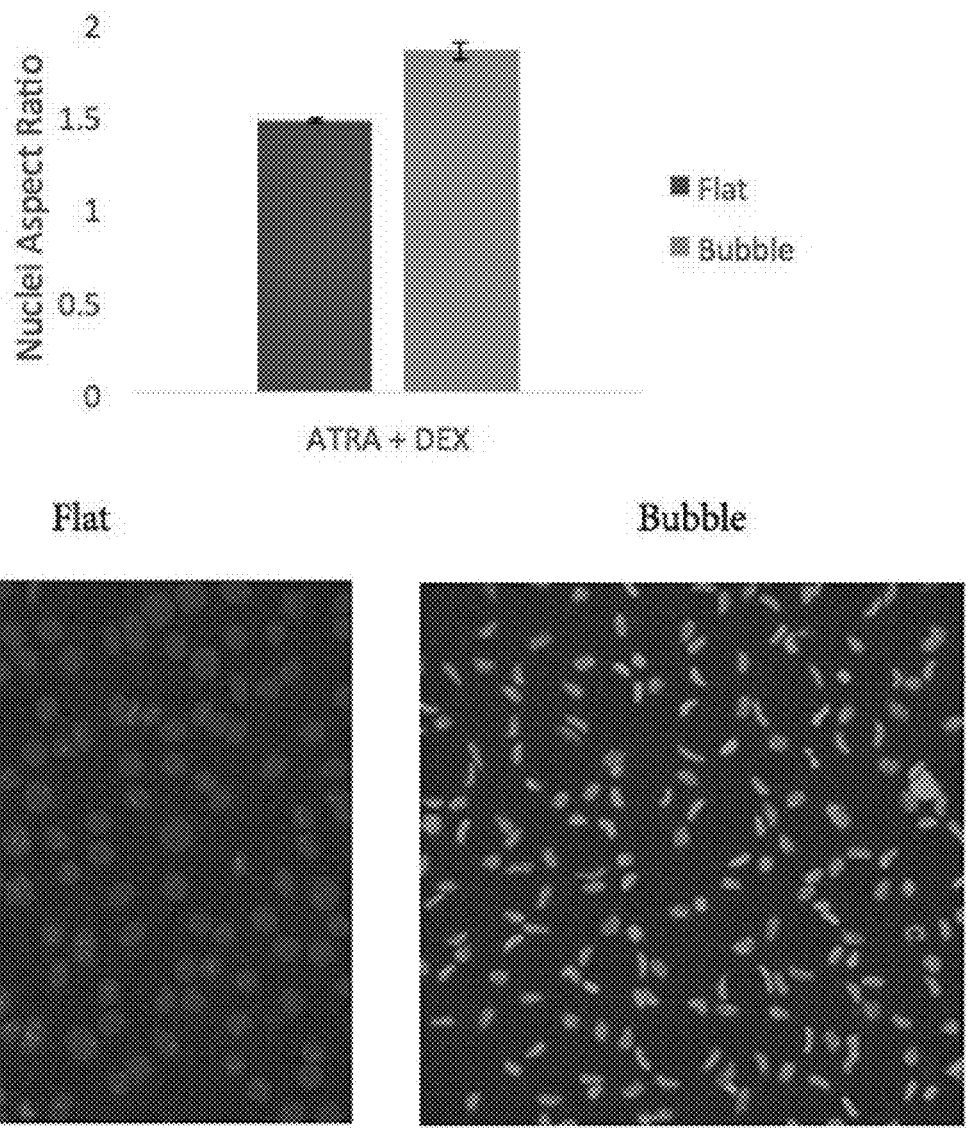
FIG. 9B shows a plot and images comparing the ratio of interdigitated to boundary length of foot processes of podocytes cultivated on a flat surface or on a microcurvature surface.

Growing evidence suggests that cell shape changes are associated with nuclear shape remodelling and regulation of genome function (31). In example studies, it was found that the presence of microcurvatures in the culture surface induces an elongation and 'bending' effect in cell nuclei, as cell nuclei get positioned in valleys between bubbles with their processes extending and wrapping around the curving microtopography. An example image of this effect is shown in FIG. 9B. FIG. 9A also shows that the ratio of interdigited to boundary length of foot processes of podocytes was significantly improved when the podocytes were cultured on the bubble surfaces compared to flat surfaced.

The above investigations demonstrated that significant nephrin gene upregulation could be achieved using biochemical and/or physical stimulation. In further investigations, modulation of the upregulated state was demonstrated, in an effort to create a model pathological system that could potentially be treated with drugs.

Puromycin amino nucleoside (PAN, Sigma-Aldrich) is a demonstrated podotoxin that is commonly used in vivo to induce proteinuria models (29). To assess how differentiated podocytes would respond to physiological insults to generate a disease model, the differentiated podocytes on the microcurvature surfaces were stimulated with various doses (17-100 µM) of PAN for 24 hours. Specifically, culture media was replaced with media containing PAN on day 8, and cell harvest was on day 9. FIG. 10A illustrates the podocyte plating, differentiation and PAN stimulation protocol timeline used in this study. Doses of 17 µM, 50 µM, and 100 µM were administered and compared to an untreated control group (5, 29). The dose-response was conducted on cells differentiated in what was found to be a highly upregulated group: namely, the cells cultivated using the disclosed apparatus with microcurvature surface, at a seeding density of 15,000 cells/cm$^2$, and in (+)ATRA media. The high dose of PAN was also administered in the (+)ATRA (+)Dex media group to confirm the ability of the system to accurately capture the protective effects of the glucocorticoid Dex.

For this range of PAN doses, a moderate downregulation of nephrin gene expression was observed compared to the PAN-free control. One-way ANOVA followed by pairwise comparisons with Fisher LSD method were used to determine the statistical significance in FIG. 10B. FIG. 10B shows results from RT-qPCR of differentiated podocytes with various PAN treatment conditions on day 9 at initial cell seeding density of 15,000 cell/cm$^2$ (average±s.d., n=3). Lines indicate significant difference between groups with $p<0.05$. The differences are considered significant at $p<0.05$ with n=>3/group to achieve a power greater than 0.90.

From immunostaining results, it appeared that cell membrane area and nephrin expression decreased, indicating a possible reduction in cell spreading as a result of the PAN insult. However, the localization of nephrin still consistently appeared on top of the bubbles. FIGS. 10C and 10D show immunostaining for nephrin and WGA of differentiated podocytes treated without (FIG. 10C) or with (FIG. 10D) 100 µM PAN (scale bar represents 100 µm, insets 50 µm).

These results suggest that topographical cues could play a stronger effect in regulating nephrin localization and expression than biochemical cues. Furthermore, the presence of microcurvature in the culture system was able to confirm the protective effect of Dex on podocytes (5) where the PAN-treated podocytes in (+)ATRA (+)Dex media showed no significant difference from the PAN-free control group (see FIG. 10B).

For high-throughput applications, a hot embossing method of fabrication may be used. To demonstrate this example fabrication technique, custom-built polystyrene cell culture plates exhibiting a surface with microcurvatures was fabricated. Polystyrene was used for this fabrication because polystyrene is the gold standard in cell culture and is inert to drug absorption.

Figure 11A:
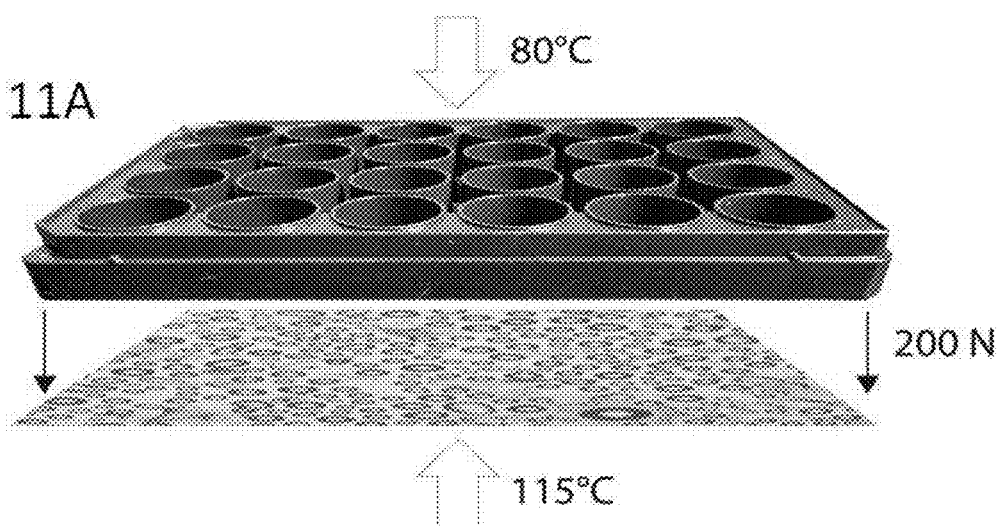
FIG. 11A illustrates an example method for fabricating a cell cultivation system using hot embossing.

The example fabrication method is illustrated in FIG. 11A. In this example, the hemispherical microfeatures of the PDMS master mold were transferred to a 1.4 mm thick sheet of clear polystyrene in a hot embosser, using a force of 500 N and temperature of 180° C. for 20 minutes. The polystyrene sheet 1102, now containing convex hemispherical microfeatures, was cut into a smaller rectangle (85 by 127 mm) in order to fit the base of a 24-well bottomless plate 1104 from Greiner Bio-One©. To bond the sheet 1102 to the bottomless plate 1104, the hot embosser pressed the two parts 1102, 1104 together with a force of 200 N for 6 minutes, at temperatures of 122° C. (to the base) and 80° C.

(to the top of the well plate). Although a particular process is described above, it should be understood that any suitable hot embossing process may be used.

Figure 11B:
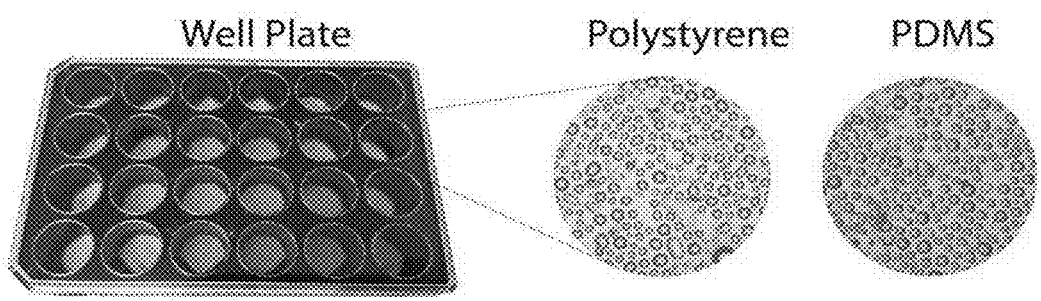
FIG. 11B illustrates an example assembled system fabricated using hot embossing.

FIG. 11B is an example of an example 24-well topographic plate 1106, produced by hot embossing, ready for cell culture.

Figure 11C:
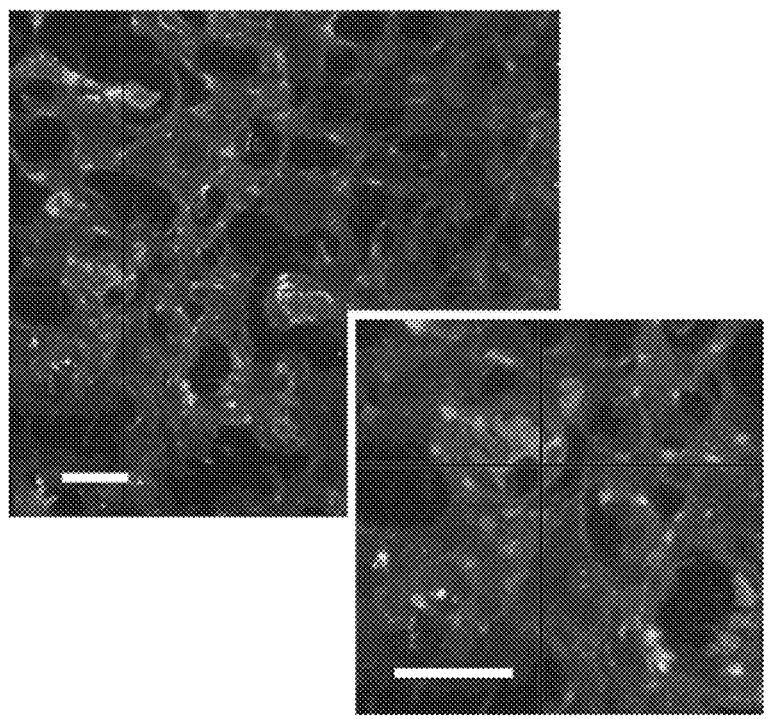
FIG. 11C shows immunostaining images for nephrin and WGA of differentiated podocytes.

The bottoms of the wells were coated with Matrigel™ prior to cell seeding. Podocytes were cultured in (+)ATRA (+)Dex media on the polystyrene plates and imaged with immunostaining and confocal, to show the consistency of results of cells grown in the polystyrene mode as compared to using PDMS inserts (see FIG. 11C). The viability of the cells and the constancy of results demonstrate the applicability of the hot embossed polystyrene plate system for cell culture.

In examples described above, Matrigel containing high content of laminin was used to coat the culture surface prior to cell seeding, to facilitate cell attachment onto the surface. Laminin and collagen IV are the major components that make up the basement membrane in between the glomerular fenestrated endothelium and podocytes. However, Matrigel is prone to batch-to-batch variation and contains various growth factors that cannot be clearly defined. To reduce variation in large-scale experiments, better chemically-defined coating solutions may be used, such as pure laminin, collagen or a combination of the two.

In examples described above, microcurvature having a radius around 50 μm was found to up-regulate nephrin expression in podocytes. In other examples, the microcurvatures may have larger or smaller radius of curvature (e.g., 5, 10 or 20 μm). For example, a radius of curvature of around 5 μm may be suitable to better mimic small capillary networks in the kidney glomerulus, where micro-vessels have diameters of only around 10 μm (37). Different radius of curvature may be achieved by using glass beads of different diameters during fabrication. For example, glass beads having diameters of 10, 20, or 40 μm may be used to achieve microcurvatures having radius of curvature of 5, 10 or 20 μm, respectively.

In some examples, the microcurvature surface may be adapted to a transwell membrane system, for example to study transfer of different compounds across a podocyte monolayer. Such a system may be used to model multiple physiological states of podocytes in response to the application of model toxins or drugs, for example.

One of the important physiological consequences from the disruption of the nephrin adhesion protein is the loss of barrier function from the podocyte slit diaphragm, which leads to abnormal protein levels in urine (e.g. albumin, etc.). The disclosed microcurvature membrane system may enable a direct measurement of the permeability of the podocyte layer in a non-invasive manner, in order to probe the barrier function at the podocyte slit diaphragm. An example of a microcurvature membrane apparatus is shown in FIGS. 12A to 12E.

Figure 12A:
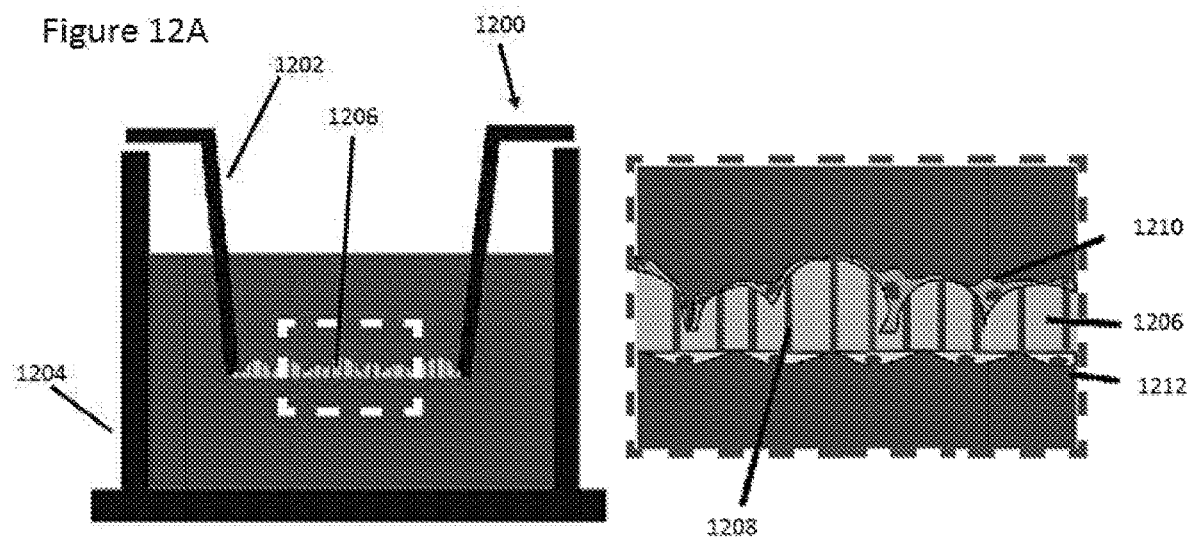
FIGS. 12A-12C illustrate an example microcurvature membrane in a transwell setup, for a co-culture system.
Figure 12A:
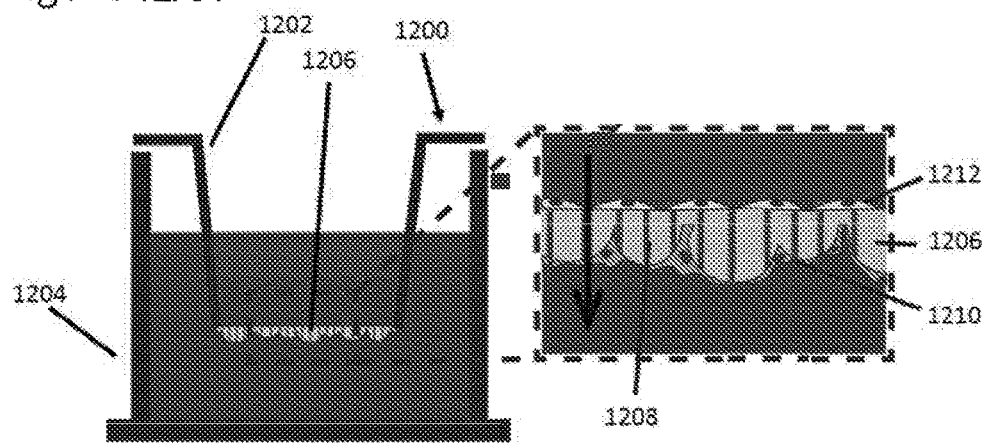

FIGS. 12A and 12AA are schematic cutaway views of an example microcurvature membrane apparatus 1200 with a cultivation surface in two different orientations. Similarly to the apparatus described with reference to FIG. 5A above, the apparatus 1200 includes a first chamber 1202 supporting a surface 1206 for cultivating cells. The first chamber 1202 has an opening to permit access to a second chamber 1204 of the apparatus. The surface 1206 in the example apparatus 1200 is positioned over the opening of the first chamber 1202 and has a porosity (e.g., about 40% nanoporosity) to permit at least partial access to the second chamber 1204. The surface 1206 has a first side and an opposing second side. Cells may be cultivated on either side of the surface. One side of the surface 1206 exhibits a first microcurvature, such as a plurality of convex microcurvatures, which may be formed as described with respect to FIG. 5A above. In the examples shown in FIG. 12A and FIG. 12AA, one side of the surface 1206 exhibits convex microcurvature and the opposite side is substantially flat. FIG. 12A shows the surface 1206 oriented with the convex microcurvatures facing upwards towards the first chamber 1202. FIG. 12AA shows the surface 1206 oriented with the convex microcurvatures facing downwards towards the second chamber 1204. The arrow indicates the direction of perfusion. The orientation of the surface 1206 may be switched depending on requisites of a particular study, for example the desired direction of perfusion (e.g., from microcurvature side to flat side or vice versa). In other examples, either side may exhibit flat, concave or convex microcurvature. As shown in the close-up view, the surface 1206 may also exhibit micro-holes 1208 (e.g., about 0.4-10 μm in diameter) that permit further fluid communication between the first and second chambers 1202, 1204, in addition to the porosity of the surface 1206. In the example shown, two types of cells are cultivated on the opposite sides of the surface 1206—podocytes 1212 may be cultivated on the side of the surface 1206 exhibiting convex microcurvature, while endothelial cells 1210 may be cultivated on the opposite side of the surface 1206.

An example technique for providing porosity in the microcurvature membrane is described further below.

To form the microcurvature surface, injection molding of a synthetic polyester elastomer, poly(octamethylene maleate (anhydride) 1,2,4-butanetricarboxylate) (called "124-polymer" (38)) may be used. In an example procedure, 124-polymer crosslinks under UV exposure. 124-polymer is synthesized by mixing 1,8-octanediol, maleic anhydride, and 1,2,4-butanetricarboxylic acid at a 5:2:3 molar ratio, melting at 140° C. and stirring for 4 hr. The resultant pre-polymer solution is then dissolved in 1,4 dioxane and purified via drop-wise precipitation in deionized distilled water. Precipitated polymer is then lyophilized. Prior to photo-crosslinking, 124-polymer is mixed with 5% (w/w) UV initiator (Irgacure 2959, Sigma). The 124-polymer solution is then injected into PDMS molds with a defined thickness (e.g., 25-50 microns) and UV cured to yield a membrane with the features of the mold.

To impart porosity into the microcurvature surface, to obtain a microcurvature membrane, an inert polymer (e.g., porogen poly(ethylene glycol) dimethyl ether, (PEGDM, Mw-500, Sigma) at 40% (w/w)) may be incorporated into the 124-polymer solution. The leaching of the porogen after UV-crosslinking of 124-polymer would reduce the bulk material density and increase its porosity. Additionally or alternatively, micro-holes (e.g., with diameters ranging from 0.4-10 microns) may be formed in the microcurvature surface to allow sufficient diffusion of small and large molecules. The micro-holes can be patterned onto the 124-polymer sheets through either a micro-fabrication technique by directly incorporating micro-posts into the mold (39), or by laser drilling for example.

The resulting microcurvature membrane may be placed into a commercially available transwell membrane insert holder. For example, the microcurvature membrane may be installed (in place of the conventional transwell membrane) by sealing the edge of the microcurvature membrane to the edge of the holder with cytocompatible glue. The resulting microcurvature transwell system may enable improved podocyte structural maturation. Other methods for fabricating the microcurvature membrane and installing the microcurvature membrane may be used. For example, FIG. 12C, discussed below, illustrates an example system for installing the microcurvature membrane without the use of glue.

Figure 12B:
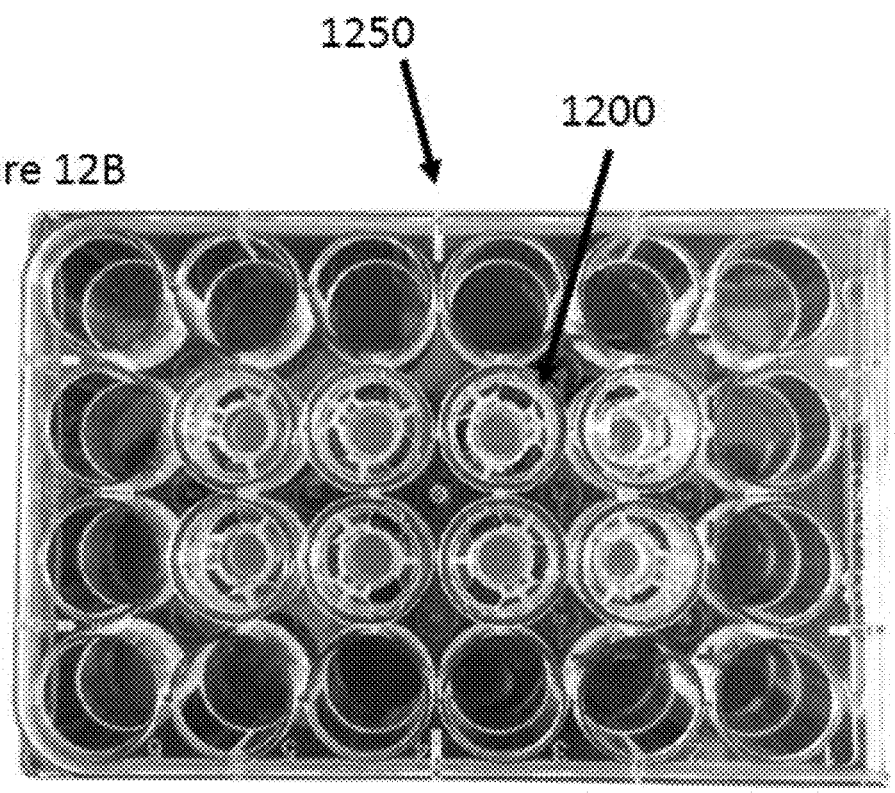
Figure 12C:
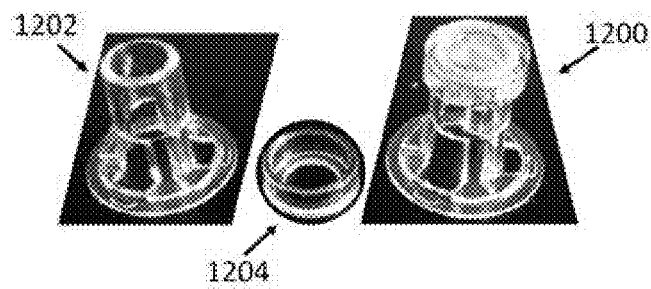

FIG. 12B is an image of an example 24-well plate 1250 in which one well is an instance of the example apparatus 1200 described above. FIG. 12C shows the components of one well disassembled. The first chamber 1202 may be formed by a transwell insert (without membrane). A cap that is fitted over the transwell insert may be used to fix the microcurvature membrane surface 1206 over the opening in the transwell insert. The assembled insert may then be positioned in the well to complete the apparatus 1200.

In some examples, other materials may be used. For example, thin PDMS or polyurethane polymer may be used, which are more mechanically stable than 124-polymer. The same micro-fabrication method and laser patterning method described above may apply to other suitable materials.

Figure 12D:
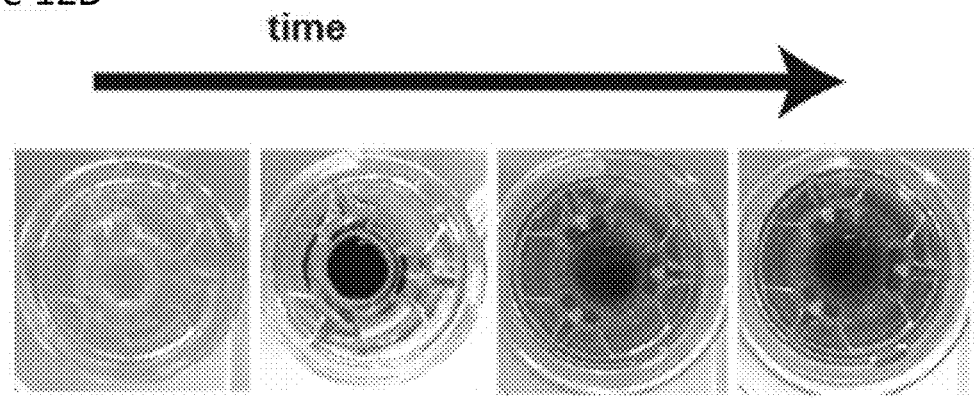
FIG. 12D shows images of diffusion of dye through a membrane using the example system of FIG. 12AA.
Figure 12E:
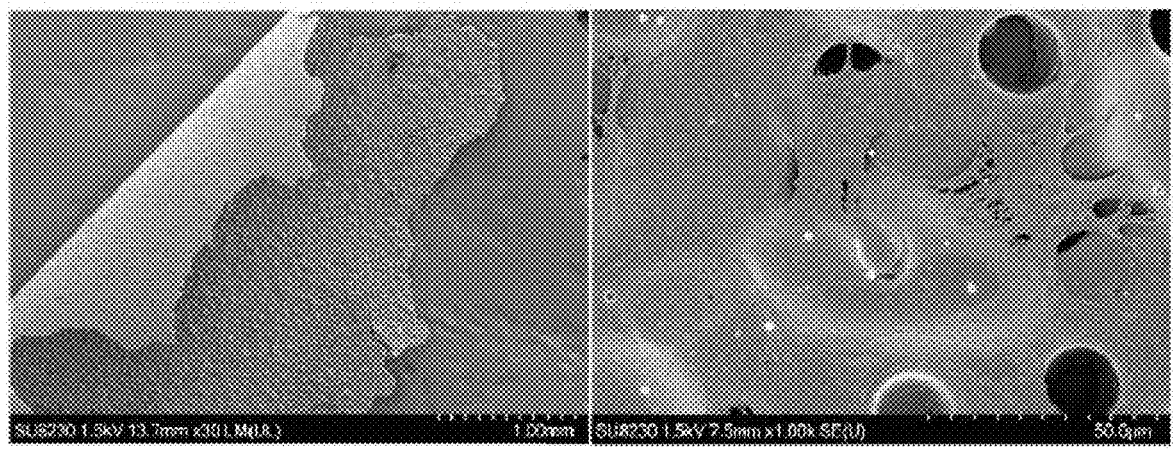
FIG. 12E shows SEM images of cell growth on an example microcurvature membrane.
Figure 12F:
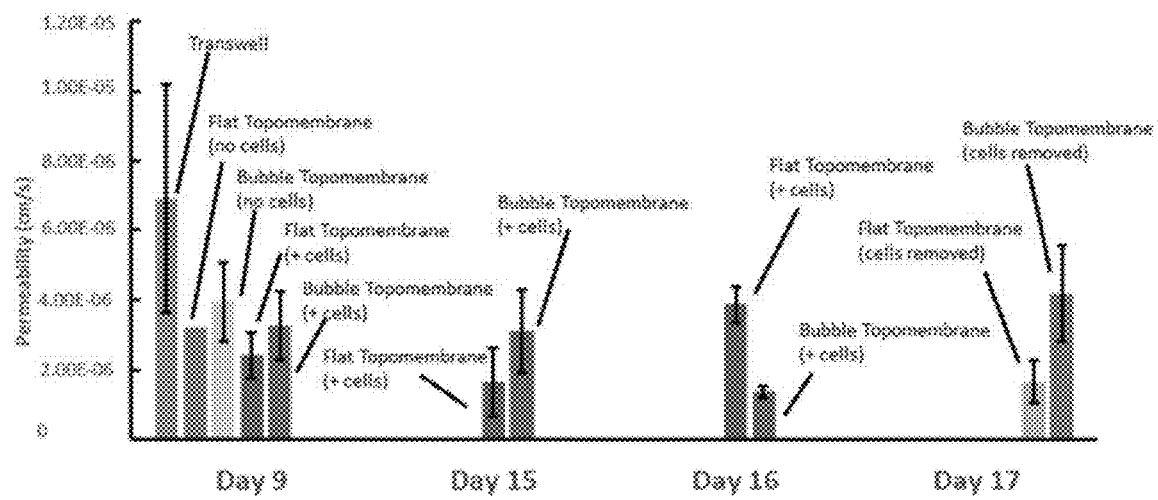
FIG. 12F is a plot comparing permeability of example cultivation membranes with different configurations.
Figure 12F:
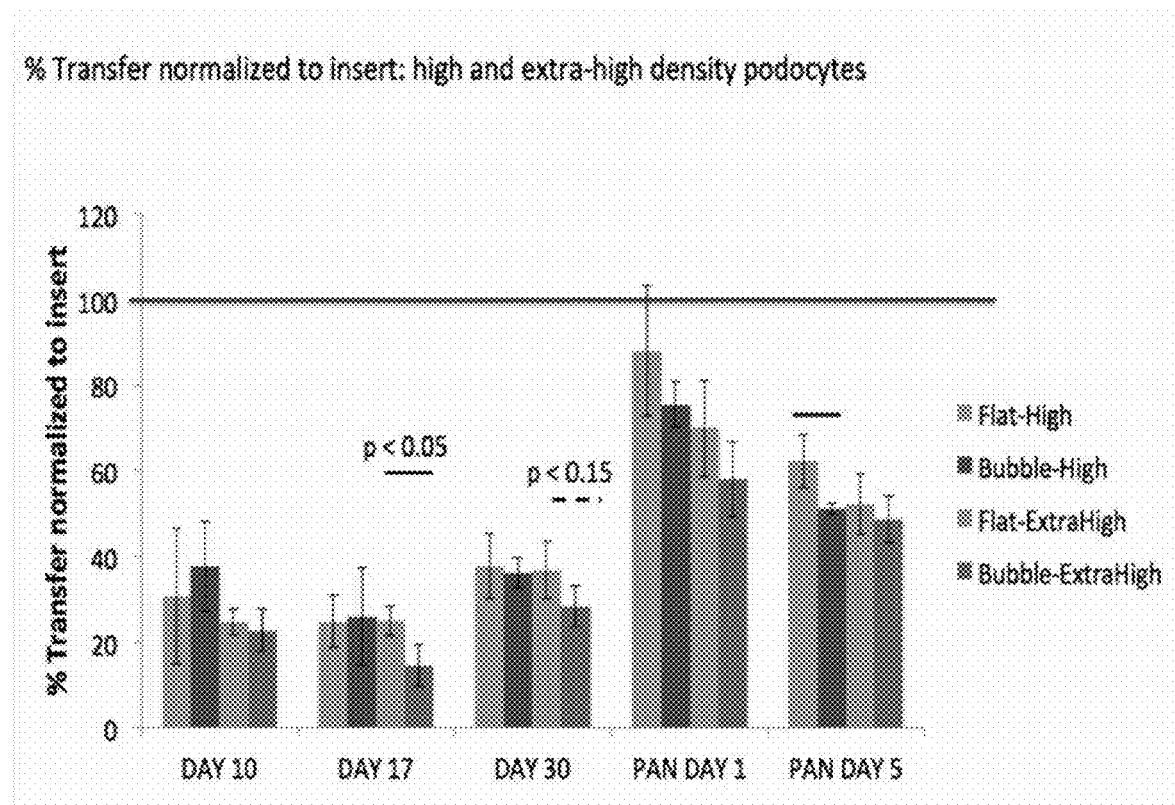

The permeability of the microcurvature membrane, without cells, may be investigated using dye, fluorescently labeled molecules, or any molecule whose concentration may be quantified in the chamber solution. Some examples include 1-10 μM of 70 kDa TRITC-dextran or 60 kDa FITC-albumin. The molecule of interest may be placed in the upper transwell chamber and collected in the lower chamber over time, or vice-versa. FIG. 12D shows images illustrating the movement of trypan blue dye from the upper chamber to the lower chamber. FIG. 12E shows SEM images of the microcurvature membrane surface with cells cultivated on the surface, showing that the cells spread to cover the micro-holes. FIG. 12F is a plot of example preliminary results showing the permeability of the membrane surface (also referred to as a "topomembrane") in different configurations, namely without microcurvature ("flat topomembrane") or with convex microcurvature ("bubble topomembrane"); with cells cultivated on the surface ("+cells"), before cell cultivation ("no cells") or after cultivated cells are removed ("cells removed"); and compared to the culture well without any membrane ("transwells"). FIG. 12FF is a plot of example results showing the permeability of cells cultured on different cultivation surfaces (flat or with microcurvature) and using different initial cell seeding density, specifically high seeding density (15,000 cells/cm$^2$) on a flat surface ("flat-high"), high seeding density on a surface with convex microcurvatures ("bubble-high"), extra-high seeding density (50,000 cells/cm$^2$) on a flat surface ("flat-extra high") and extra-high seeding density on a surface with convex microcurvatures ("bubble-extra high"). The graph shows that the cells respond to chemical insults (treatment by PAN) by increasing permeability. The cells cultivated on the microcurvature surface exhibited lower permeability than those cultivated on the flat surface, indicating that a tighter cell barrier was formed by the cells cultivated on the microcurvature surface.

In some examples, the microcurvature surface may exhibit non-planar microtopology (e.g., convex microcurvatures) on one side, and a substantially planar surface on the opposite side. In other examples, both sides may have non-planar microtopology. For example, the microcurvature surface may exhibit convex microcurvature features on one side and concave features on the opposite side. The presence of concave microcurvature on the opposite side may provide topographical stimulation for a co-culture on the opposite side. Suitable methods for providing non-planar microtopology on both sides of the surface may include, for example, spin coating or use of a mold with alignment of two topographic sheets.

For example, the presence of microcurvatures on both sides of the culture surface may be used for an endothelial-podocyte co-culture system. Endothelial cells may be seeded on the opposite side of the podocyte layer. Glomerular endothelial cells are fenestrated and phenotypically distinct to endothelial cells from other anatomical locations. To perform the co-culture, the microcurvature surface may be placed with convex surface upwards and temporarily placed in a 12-well plate. Podocytes, suspended in podocyte growth media, may be placed on the membrane for at least 2 hr to allow cell attachment. Then, the attached epithelial cell layer may be washed and the surface flipped with convex surface downwards and placed into the original 24 well plate. Then, the other cell type, e.g. endothelial cells, suspended in endothelial growth media (e.g. EGM2), may be seeded on the opposite side of the membrane. An array of custom inserts may be 3D printed to make the system more amenable to high-throughput dual cell seeding. The array of inserts may be connected together and therefore may be handled together to minimize the time spent flipping each insert one at a time. Podocytes may be seeded on the convex side of the microcurvature membrane. During co-culture, endothelial growth media or another suitable co-culture medium may be used.

In some examples, electrospinning techniques may be used with biocompatible materials to produce thin rounded fibers of a desired radius. Such fibers may be randomly placed, as a fibrous cushion, onto the transwell inserts. Such a fibrous mesh may be relatively easy to fabricate and may provide a 3D environment suitably dense with curvature, as in the glomerulus.

Figure 13:
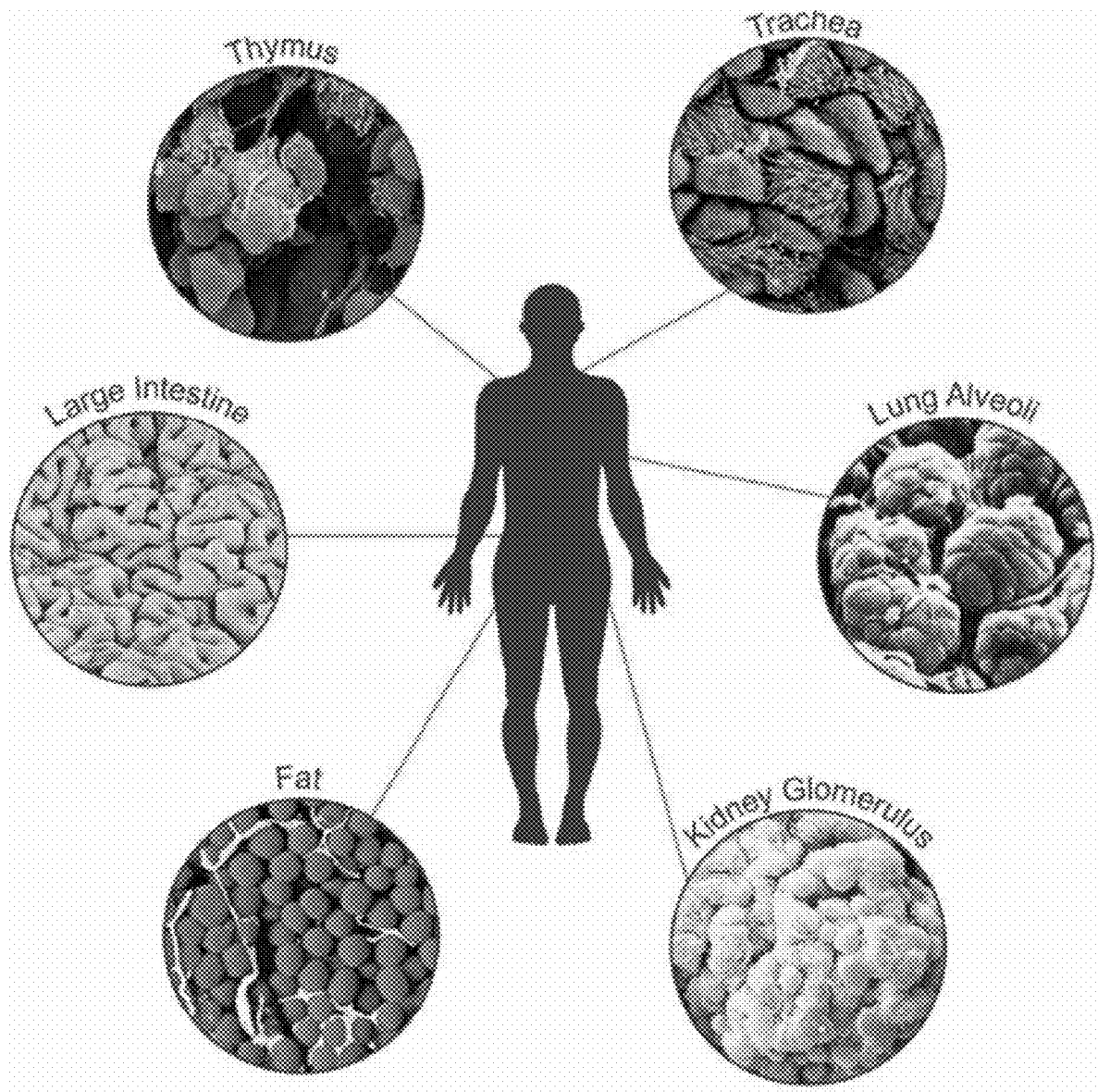
FIG. 13 is a diagram illustrating curvature-filled microenvironments throughout the human body.

Although examples have been described in the context of podocytes, the present disclosure may be applicable to cultivation of other cells. Many cells in vivo experience an out-of-plane curvature. For example, blood vessels and capillaries are cylindrical, and alveoli are spherical. There is growing evidence that physical geometry is an important factor in the development and function of cells (42). For example, cardiac tissues may be guided using spatial factors such as grooves and topographic patterning that mimic native cardiac anisotropy (18, 19). Epithelial tissues also have different migration patterns and properties when growing around cylindrical wires of varying radii due to cytoskeletal rearrangements (27). Examples of the disclosed system may thus be suitable for the culture of many different cell types throughout the body. Some examples are shown in FIG. 13.

In examples disclosed herein, it was demonstrated that topographic cues, for example as provided by a microcurvature surface, induce differentiating behaviour in podocytes. In example studies, podocytes cultured on the microcurvature platform showed: enhanced nephrin expression, localization of nephrin to curved surfaces, greater arborisation, and increased cell spreading. The incorporation of curvature effects thus was found to influence cell development. Localization of nephrin to intercellular junctions was consistently seen on the tops of microcurvature surfaces where multiple podocytes often wrap and form inter-cellular junctions over the microcurvature structure. These differences in morphology correlated with the curvature-induced upregulation of nephrin gene expression, and are a clear indication of podocyte differentiation.

The non-planar microtopology may challenge the cells to express and localize adhesion proteins to the curved areas, which determines cytoskeletal rearrangements (9, 32-34). The nuclear distortion that occurs as cells wrap around protruding microhemispheres may be another factor that affects cell behaviour. This strategic, mechanically induced positioning of cells is similar to how podocytes appear in the native glomerulus with cell nuclei/bodies cushioned in the valleys and their processes wrapped around globular capillary beds.

In example studies, it was found that differentiated podocytes display not only enhanced upregulation of nephrin gene expression in response to both surface micro-curvature and hormonal and vitamin supplementation, but also downregulation in response to insult. The disclosed microcurvature cultivation platform thus exhibited sensitivity to detect both types of effects, which may enable it to be used to model both healthy and diseased states. Where topography and biochemical stimulation can upregulate nephrin expression, PAN-induced insults showed dose-response downregulated behaviour. Furthermore, the system was found to accurately respond to treatment effects, such as when Dex was administered prior to high dosages of PAN, whereby the culture system demonstrated the protective effects of the glucocorticoid.

The present disclosure also described an example fabrication technique to incorporate out-of-plane curvature onto a 2D surface for creating a biomimetic environment for cell culture. The example technique may be scalable and may be readily adaptable to a standard multi-well plate format for ease of use and rapid translation to the established industrial drug screening process that is based on commercial well plates. In an example, hot embossing was used to custom-build polystyrene 24-well cell culture plates with a microcurvature surface. The resulting apparatus may be gamma ray sterilized, packaged, and may be used in high-throughput commercial applications. Polystyrene is inert, compatible with drug testing, and it can be used directly with fluorescent imaging as well as with high content imaging stations.

Although the present disclosure presents examples in which immortalized animal cell lines were used, the disclosed methods and apparatus may be suitable for cultivation of other cells types, including other podocyte cell types (e.g., primary podocytes from animals or humans, or stem-cell derived podocytes).

In some examples described herein, the cell culture surface was provided with randomly distributed microcurvatures. In other examples, the placement of microcurvatures may be at selected locations. For example, 3D printing could be used to print out-of plane grids with curved walls where podocyte cell bodies can sit within shallow valleys while their processes extend out to form slit diaphragms with neighbouring cells.

The present disclosure also describes an example apparatus for co-culture of cells, for example podocytes with endothelium.

The present disclosure may be applicable for commercial uses, such as to perform studies for drug discovery, including drugs aimed at kidney therapy and proteinuria treatments, as well as other compounds that may affect the kidney. Other organs (e.g., as illustrated in FIG. 13) may also be investigated using the example methods and apparatuses disclosed herein.

An example 1 of the present disclosure provides an apparatus for cultivation of cells, the apparatus comprising: a first chamber for cultivating cells; and a surface, supported in the first chamber, for cell cultivation thereon, the surface exhibiting at least one microcurvature providing a non-planar microtopology.

An example 2 of the present disclosure provides the apparatus of example 1, wherein the at least one microcurvature is a convex microcurvature.

An example 3 of the present disclosure provides the apparatus of example 1, wherein the at least one microcurvature is a concave microcurvature.

An example 4 of the present disclosure provides the apparatus of any one of examples 1 to 3, wherein the first chamber has an opening defined therein to permit access to a second chamber, and wherein the surface is positioned over the opening and has a porosity to enable at least partial access to the second chamber.

An example 5 of the present disclosure provides the apparatus of example 4, wherein the porosity is about 40%.

An example 6 of the present disclosure provides the apparatus of example 4 or 5, wherein the surface comprises a first side exhibiting a first microcurvature and an opposing second side exhibiting a second microcurvature.

An example 7 of the present disclosure provides the apparatus of example 6, wherein the first microcurvature includes a convex microcurvature and the second microcurvature includes a concave microcurvature.

An example 8 of the present disclosure provides the apparatus of example 4 or 5, wherein the surface comprises a first side exhibiting a convex microcurvature and an opposing second side that is substantially flat.

An example 9 of the present disclosure provides the apparatus of example 4, wherein at least one micro-hole is defined in the surface, to permit further access to the second chamber.

An example 10 of the present disclosure provides the apparatus of example 9, wherein the at least one micro-hole has a diameter in the range of about 0.4-10 µm.

An example 11 of the present disclosure provides the apparatus of any one of examples 1 to 10, wherein the at least one microcurvature has an average diameter of about 20-100 µm and a height of about 5-20 µm.

An example 12 of the present disclosure provides the apparatus of any one of examples 1 to 10, wherein the at least one microcurvature has a radius of curvature of about 5, 10, 50 or 20 µm.

An example 13 of the present disclosure provides the apparatus of any one of examples 1 to 12, wherein the surface comprises a plurality of convex microcurvatures.

An example 14 of the present disclosure provides a method for cultivating cells, the method comprising: providing the apparatus of any one of examples 1 to 13; introducing cells onto the surface of the apparatus; and promoting differentiation of the cells.

An example 15 of the present disclosure provides the method of example 14 wherein the cells are podocytes.

An example 16 of the present disclosure provides a method for fabricating an apparatus for cultivation of cells, the method comprising: providing a bead-covered surface by fixing a plurality of glass beads on a substrate; forming an inverse mold by curing a first polymer over the bead-covered surface; forming a surface for cell cultivation by curing a second polymer using the inverse mold, the surface being formed to exhibit at least one microcurvature providing a non-planar microtopology; and supporting at least a portion of the surface in a first chamber for cultivating cells.

An example 17 of the present disclosure provides the method of example 16, wherein the plurality of glass beads includes glass beads having diameters in the range of about 10-1000 µm.

An example 18 of the present disclosure provides the method of example 16 or 17, wherein the plurality of glass beads includes glass beads having diameters of 10, 20, or 40 μm.

An example 19 of the present disclosure provides the method of any one of examples 16 to 18, wherein the plurality of glass beads includes glass beads having varying diameters.

An example 20 of the present disclosure provides the method of any one of examples 16 to 18, wherein the plurality of glass beads all have similar diameter.

An example 21 of the present disclosure provides the method of any one of examples 16 to 20, wherein the glass beads are fixed on the substrate in an organized fashion.

An example 22 of the present disclosure provides the method of any one of examples 16 to 20, wherein the glass beads are fixed on the substrate in a random fashion.

An example 23 of the present disclosure provides the method of any one of examples 16 to 22, wherein the second polymer comprises polydimethylsiloxane (PDMS) or poly(octamethylene maleate (anhydride) 1,2,4-butanetricarboxylate (124-polymer).

An example 24 of the present disclosure provides the method of example 23, wherein the second polymer is 124-polymer with an inert polymer incorporated therein, the method further comprising leaching out the inert polymer after curing.

An example 25 of the present disclosure provides the method of any one of examples 16 to 24, further comprising forming micro-holes in the surface.

An example A1 of the present disclosure provides an apparatus for cultivation of cells, the apparatus comprising: a first chamber for cultivating cells; and a mesh, supported in the first chamber, for cell cultivation thereon, the mesh comprising a network of strands.

An example A2 of the present disclosure provides the apparatus of example A1, wherein the first chamber has an opening defined therein to permit access to a second chamber, and wherein the mesh is positioned over the opening and has a porosity to enable at least partial access to the second chamber.

An example A3 of the present disclosure provides the apparatus of example A2, wherein the porosity is about 40%.

An example A4 of the present disclosure provides the apparatus of any one of examples A1 to A3, wherein the strands of the mesh each has a radius of curvature of about 5, 10 or 20 μm.

An example A5 of the present disclosure provides the apparatus of any one of examples A1 to A4, wherein the mesh comprises a regularly organized network of strands.

An example A6 of the present disclosure provides the apparatus of any one of examples A1 to A4, wherein the mesh comprises a randomly organized network of strands.

An example A7 of the present disclosure provides the apparatus of any one of examples A1 to A6, wherein the mesh comprises a micro-mesh.

An example A8 of the present disclosure provides the apparatus of any one of examples A1 to A7, wherein the mesh provides a non-planar microtopology for cultivating cells.

An example A9 of the present disclosure provides the apparatus of any one of examples A1 to A8, wherein each strand has an outer surface exhibiting convex microcurvature.

An example B1 of the present disclosure provides a method for cultivating cells, the method comprising: seeding podocytes on a cell cultivation surface at a seeding density; introducing differentiation media to the podocytes, the differentiation media including all-trans-retinoic acid (ATRA), 1,25-dihydroxy vitamin D3 (Vit D3), and dexamethasone (Dex); removing Dex from the differentiation media after a first time duration; and obtaining cultivated cells after a second time duration.

An example B2 of the present disclosure provides the method of example B1, wherein the cell cultivation surface exhibits at least one microcurvature providing a non-planar topology.

An example B3 of the present disclosure provides the method of example B2, wherein the at least one microcurvature is a convex microcurvature.

An example B4 of the present disclosure provides the method of example B2, wherein the at least one microcurvature is a concave microcurvature.

An example B5 of the present disclosure provides the method of any one of examples B1 to B4, wherein the surface has a porosity to enable at least partial communication between a first side of the surface and an opposing second side of the surface.

An example B6 of the present disclosure provides the method of example B5, wherein the porosity is about 40%.

An example B7 of the present disclosure provides the method of example B5 or B6, wherein the first side exhibits a first microcurvature and the second side exhibits a second microcurvature.

An example B8 of the present disclosure provides the method of example B7, wherein the first microcurvature is a convex microcurvature and the second microcurvature is a concave microcurvature.

An example B9 of the present disclosure provides the method of example B5 or B6, wherein the first side exhibits a convex microcurvature and the second side is substantially flat.

An example B10 of the present disclosure provides the method of any one of examples B1 to B9, wherein at least one micro-hole is defined in the surface.

An example B11 of the present disclosure provides the method of example B10, wherein the at least one micro-hole has a diameter in the range of about 0.4-10 μm.

An example B12 of the present disclosure provides the method of any one of examples B2 to B11, wherein the at least one microcurvature has an average diameter of about 20-100 μm and a height of about 5-20 μm.

An example B13 of the present disclosure provides the method of any one of examples B2 to B11, wherein the at least one microcurvature has a radius of curvature of about 5, 10, 50 or 20 μm.

An example B14 of the present disclosure provides the method of any one of examples B2 to B13, wherein the surface comprises a plurality of convex microcurvatures.

An example B15 of the present disclosure provides the method of example B1, wherein the cell cultivation surface comprises a mesh comprising a network of strands.

An example B16 of the present disclosure provides the method of example B15, wherein the strands of the mesh each has a radius of curvature of about 5, 10 or 20 μm.

An example B17 of the present disclosure provides the method of example B15 or B16, wherein the mesh comprises a regularly organized network of strands.

An example B18 of the present disclosure provides the method of example B15 or B16, wherein the mesh comprises a randomly organized network of strands.

An example B19 of the present disclosure provides the method of any one of examples B15 to B18, wherein the mesh comprises a micromesh.

An example B20 of the present disclosure provides the method of any one of examples B15 to B19, wherein the mesh provides a non-planar microtopology for cultivating cells.

An example B21 of the present disclosure provides the method of any one of examples B15 to B20, wherein each strand has an outer surface exhibiting convex microcurvature.

An example B22 of the present disclosure provides the method of any one of examples B1 to B21, wherein ATRA is introduced at a concentration of 200 nM, Vit D3 is introduced at a concentration of 10 nM, and Dex is introduced at a concentration of 100 nM.

An example B23 of the present disclosure provides the method of any one of examples B1 to B22, wherein the seeding density is 50,000 cells/cm$^2$.

An example B24 of the present disclosure provides the method of any one of examples B1 to B23, wherein the first time duration is 2 days.

An example B25 of the present disclosure provides the method of any one of examples B1 to B24, wherein the second time duration is in the range of about 9 days to about 14 days.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

1. Burghardt T, Hochapfel F, Salecker B, Meese C, Grone H J, Rachel R, et al. Advanced electron microscopic techniques provide a deeper insight into the peculiar features of podocytes. American journal of physiology Renal physiology. 2015; 309(12): F1082-9.
2. Shankland S J, Pippin J W, Reiser J, Mundel P. Podocytes in culture: past, present, and future. Kidney Int. 2007; 72(1):26-36.
3. Li M, Corbelli A, Watanabe S, Armelloni S, Ikehata M, Parazzi V, et al. Three-dimensional podocyte-endothelial cell co-cultures: Assembly, validation, and application to drug testing and intercellular signaling studies. European journal of pharmaceutical sciences: official journal of the European Federation for Pharmaceutical Sciences. 2016; 86:1-12.
4. Bruggeman L A, Doan R P, Loftis J, Darr A, Calabro A. A cell culture system for the structure and hydrogel properties of basement membranes; Application to capillary walls. Cellular and molecular bioengineering. 2012; 5(2):194-204.
5. Ransom R F, Lam N G, Hallett M A, Atkinson S J, Smoyer W E. Glucocorticoids protect and enhance recovery of cultured murine podocytes via actin filament stabilization. Kidney Int. 2005; 68(6):2473-83.
6. Vaughan M R, Pippin J W, Griffin S V, Krofft R, Fleet M, Haseley L, et al. ATRA induces podocyte differentiation and alters nephrin and podocin expression in vitro and in vivo. Kidney Int. 2005; 68(1):133-44.
7. Takano Y, Yamauchi K, Hiramatsu N, Kasai A, Hayakawa K, Yokouchi M, et al. Recovery and maintenance of nephrin expression in cultured podocytes and identification of HGF as a repressor of nephrin. American journal of physiology Renal physiology. 2007; 292(5):F1573-82.
8. Chittiprol S, Chen P, Petrovic-Djergovic D, Eichler T, Ransom R F. Marker expression, behaviors, and responses vary in different lines of conditionally immortalized cultured podocytes. American journal of physiology Renal physiology. 2011; 301(3):F660-71.
9. Schiwek D, Endlich N, Holzman L, Holthofer H, Kriz W, Endlich K. Stable expression of nephrin and localization to cell-cell contacts in novel murine podocyte cell lines. Kidney Int. 2004; 66(1):91-101.
10. Takasato M, Pei X E, Chiu H S, Maier B, Baillie G J, Ferguson C, et al. Kidney organoids from human iPS cells contain multiple lineages and model human nephrogenesis. Nature. 2015; 526(7574):564-8.
11. Kawachi H, Miyauchi N, Suzuki K, Han G D, Orikasa M, Shimizu F. Role of podocyte slit diaphragm as a filtration barrier. Nephrology (Carlton). 2006; 11(4):274-81.
12. Brinkkoetter P T, Ising C, Benzing T. The role of the podocyte in albumin filtration. Nature reviews Nephrology. 2013; 9(6):328-36.
13. Herman-Edelstein M, Thomas M C, Thallas-Bonke V, Saleem M, Cooper M E, Kantharidis P. Dedifferentiation of immortalized human podocytes in response to transforming growth factor-beta: a model for diabetic podocytopathy. Diabetes. 2011; 60(6):1779-88.
14. Obregon R, Ramon-Azcon J, Ahadian S, Shiku H, Bae H, Ramalingam M, et al. The use of microtechnology and nanotechnology in fabricating vascularized tissues. Journal of nanoscience and nanotechnology. 2014; 14(1):487-500.
15. Au H T H, Cheng I, Chowdhury M F, Radisic M. Interactive effects of surface topography and pulsatile electrical field stimulation on orientation and elongation of fibroblasts and cardiomyocytes. Biomaterials. 2007; 28(29):4277-93.
16. Chiu L L Y, Montgomery M, Liang Y, Liu H, Radisic M. Perfusable branching microvessel bed for vascularization of engineered tissues. Proceedings of the National Academy of Sciences of the United States of America. 2012; 109(50):E3414-E23.
17. Zhang B, Montgomery M, Chamberlain M D, Ogawa S, Korolj A, Pahnke A, et al. Biodegradable scaffold with built-in vasculature for organ-on-a-chip engineering and direct surgical anastomosis. Nature materials. 2016.
18. Pahnke A, Montgomery M, Radisic M. Spatial and Electrical Factors Regulating Cardiac Regeneration and Assembly. 2015:71-92.
19. Engelmayr G C, Jr., Cheng M, Bettinger C J, Borenstein J T, Langer R, Freed L E. Accordion-like honeycombs for tissue engineering of cardiac anisotropy. Nature materials. 2008; 7(12):1003-10.

20. Zhang B, Montgomery M, Davenport-Huyer L, Korolj A, Radisic M. Platform technology for scalable assembly of instantaneously functional mosaic tissues. Science Advances. 2015; 1(7).
21. Bhatia S N, Ingber D E. Microfluidic organs-on-chips. Nature biotechnology. 2014; 32(8):760-72.
22. Mu X, Zheng W, Xiao L, Zhang W, Jiang X. Engineering a 3D vascular network in hydrogel for mimicking a nephron. Lab on a Chip. 2013; 13(8):1612.
23. Li M, Hakimi N, Perez R, Waldman S, Kozinski J A, Hwang D K. Microarchitecture for a three-dimensional wrinkled surface platform. Advanced materials (Deerfield Beach, Fla.). 2015; 27(11):1880-6.
24. Kang E, Shin S-J, Lee K H, Lee S-H. Novel PDMS cylindrical channels that generate coaxial flow, and application to fabrication of microfibers and particles. Lab on a Chip. 2010; 10(14):1856-61.
25. Park J Y, Lee D H, Lee E J, Lee S-H. Study of cellular behaviors on concave and convex microstructures fabricated from elastic PDMS membranes. Lab on a Chip. 2009; 9(14):2043-9.
26. Hosseini V, Kollmannsberger P, Ahadian S, Ostrovidov S, Kaji H, Vogel V, et al. Fiber-assisted molding (FAM) of surfaces with tunable curvature to guide cell alignment and complex tissue architecture. Small (Weinheim an der Bergstrasse, Germany). 2014; 10(23):4851-7.
27. Yevick H G, Duclos G, Bonnet I, Silberzan P. Architecture and migration of an epithelium on a cylindrical wire. Proceedings of the National Academy of Sciences of the United States of America. 2015; 112(19):5944-9.
28. Schmittgen T D, Livak K J. Analyzing real-time PCR data by the comparative CT method. Nature Protocols. 2008; 3(6):1101-8.
29. Guan N, Ding J, Deng J, Zhang J, Yang J. Key molecular events in puromycin aminonucleoside nephrosis rats. Pathology international. 2004; 54(9):703-11.
30. Wiedeman M P. Dimensions of blood vessels from distributing artery to collecting vein. Circulation Research. 1963; 12(4):375-8.
31. Versaevel M, Grevesse T, Gabriele S. Spatial coordination between cell and nuclear shape within micropatterned endothelial cells. Nat Commun. 2012; 3:671.
32. George B, Verma R, Soofi A A, Garg P, Zhang J, Park T J, et al. Crk½-dependent signaling is necessary for podocyte foot process spreading in mouse models of glomerular disease. The Journal of clinical investigation. 2012; 122(2):674-92.
33. Schwarz K, Simons M, Reiser J, Saleem M A, Faul C, Kriz W, et al. Podocin, a raft-associated component of the glomerular slit diaphragm, interacts with CD2AP and nephrin. The Journal of clinical investigation. 2001; 108 (11):1621-9.
34. Garg P, Holzman L B. Podocytes: gaining a foothold. Experimental cell research. 2012; 318(9):955-63.
35. von Philipsborn A C, Lang S, Bernard A, Loeschinger J, David C, Lehnert D, et al. Microcontact printing of axon guidance molecules for generation of graded patterns. Nat Protocols. 2006; 1(3):1322-8.
36. Saleem M A, O'Hare M J, Reiser J, Coward R J, Inward C D, Farren T, et al. A Conditionally Immortalized Human Podocyte Cell Line Demonstrating Nephrin and Podocin Expression. Journal of the American Society of Nephrology. 2002; 13(3):630-8.
37. Haraldsson B, Nystrom J, Deen W M. Properties of the glomerular barrier and mechanisms of proteinuria. Physiol Rev. 2008; 88(2):451-87.
38. Davenport Huyer L, Zhang B, Korolj A, Montgomery M, Drecun S, Conant G, et al. Highly Elastic and Moldable Polyester Biomaterial for Cardiac Tissue Engineering Applications. ACS Biomaterials Science & Engineering. 2016; 2(5):780-8.
39. Zhang B, Montgomery M, Chamberlain M D, Ogawa S, Korolj A, Pahnke A, et al. Biodegradable scaffold with built-in vasculature for organ-on-a-chip engineering and direct surgical anastomosis. Nat Mater. 2016; 15(6):669-78.
40. Gaillard P J, Voorwinden L H, Nielsen J L, Ivanov A, Atsumi R, Engman H, et al. Establishment and functional characterization of an in vitro model of the blood-brain barrier, comprising a co-culture of brain capillary endothelial cells and astrocytes. Eur J Pharm Sci. 2001; 12(3):215-22.
41. Yuan W, Lv Y, Zeng M, Fu B M. Non-invasive measurement of solute permeability in cerebral microvessels of the rat. Microvascular research. 2009; 77(2):166-73.
42. Zadpoor A A. Bone tissue regeneration: the role of scaffold geometry. Biomaterials science. 2015; 3(2):231-45.
43. Unger, M. A., Chou, H. P., Thorsen, T., Scherer, A. & Quake, S. R. Monolithic microfabricated valves and pumps by multilayer soft lithography. *Science* 288, 113-116 (2000).

The invention claimed is:

1. An apparatus for cultivation of cells, the apparatus comprising:
   a first chamber for cultivating cells; and
   a surface, supported in the first chamber, for cell cultivation thereon, the surface exhibiting a plurality of hemispherical features, each hemispherical feature being an out-of-plane hemispherical microcurvature providing a non-planar microtopology for the surface, the plurality of hemispherical features including hemispherical features of different diameters and heights.

2. The apparatus of claim 1, wherein the plurality of hemispherical features includes at least one out-of-plane hemispherical microcurvature that is a convex microcurvature.

3. The apparatus of claim 1, wherein the plurality of hemispherical features includes at least one out-of-plane hemispherical microcurvature that is a concave microcurvature.

4. The apparatus of claim 1, wherein the first chamber has an opening defined therein to permit access to a second chamber, and wherein the surface is positioned over, parallel or perpendicular to the opening and has a porosity to enable at least partial access to the second chamber.

5. The apparatus of claim 4, wherein the porosity is about 40%.

6. The apparatus of claim 4, wherein the surface comprises a first side exhibiting a first plurality of hemispherical features including out-of-plane hemispherical microcurvatures and an opposing second side exhibiting a second plurality of hemispherical features including out-of-plane hemispherical microcurvatures.

7. The apparatus of claim 6, wherein the first plurality of hemispherical features includes a convex microcurvature and the second plurality of hemispherical features includes a concave microcurvature.

8. The apparatus of claim 4, wherein the surface comprises a first side exhibiting a first plurality of hemispherical features including a convex microcurvature and an opposing second side that is substantially flat.

9. The apparatus of claim 4, wherein at least one micro-hole is defined in the surface, to permit further access to the second chamber.

10. The apparatus of claim 9, wherein the at least one micro-hole has a diameter in the range of about 0.4-10 µm.

11. The apparatus of claim 1, wherein the plurality of hemispherical features includes at least one out-of-plane hemispherical microcurvature that has an average diameter of about 10-100 µm and a height of about 5-40 µm.

12. The apparatus of claim 1, wherein the plurality of hemispherical features includes at least one out-of-plane hemispherical microcurvature that has a radius of curvature of about 5, 10, 50 or 20 µm.

13. The apparatus of claim 1, wherein the plurality of hemispherical features comprises a plurality of convex out-of-plane hemispherical microcurvatures.

14. A method for cultivating cells, the method comprising:
providing an apparatus comprising:
a first chamber for cultivating cells; and
a surface, supported in the first chamber, for cell cultivation thereon, the surface exhibiting a plurality of hemispherical features, each hemispherical feature being an out-of-plane hemispherical microcurvature providing a non-planar microtopology for the surface, the plurality of hemispherical features including hemispherical features of different diameters and heights;
introducing cells onto the surface of the apparatus; and
promoting differentiation of the cells.

15. The method of claim 14 wherein the cells are podocytes.

16. A method for fabricating an apparatus for cultivation of cells, the method comprising:
providing a bead-covered surface by fixing a plurality of glass beads on a substrate, the plurality of glass beads including spherical beads of different diameters;
forming an inverse mold by curing a first polymer over the bead-covered surface;
forming a surface for cell cultivation by curing a second polymer using the inverse mold, the surface being formed to exhibit a plurality of hemispherical features, each hemispherical feature being an out-of-plane hemispherical microcurvature providing a non-planar microtopology for the surface, the plurality of hemispherical features including hemispherical features of different diameters and heights; and
supporting at least a portion of the surface in a first chamber for cultivating cells.

17. The method of claim 16, wherein the plurality of glass beads includes glass beads having diameters in the range of about 10-1000 µm.

18. The method of claim 16, wherein the plurality of glass beads includes glass beads having diameters of 10, 20, or 40 µm.

19. The method of claim 16, wherein the glass beads are fixed on the substrate in an organized fashion.

20. The method of claim 16, wherein the glass beads are fixed on the substrate in a random fashion.

21. The method of claim 16, wherein the second polymer comprises polydimethylsiloxane (PDMS), polystyrene, or poly(octamethylene maleate (anhydride) 1,2,4-butanetricarboxylate) (124-polymer).

22. The method of claim 21, wherein the second polymer is 124-polymer with an inert polymer incorporated therein, the method further comprising leaching out the inert polymer after curing.

23. The method of claim 16, further comprising forming micro-holes in the surface.

* * * * *